(12) United States Patent
Chade, III et al.

(10) Patent No.: US 10,322,189 B2
(45) Date of Patent: Jun. 18, 2019

(54) KIDNEY-TARGETED DRUG DELIVERY SYSTEMS

(71) Applicant: University of Mississippi Medical Center, Jackson, MS (US)

(72) Inventors: Alejandro R. Chade, III, Brandon, MS (US); Gene L. Bidwell, III, Jackson, MS (US)

(73) Assignee: University of Mississippi Medical Center, Jackson, MS (US)

( * ) Notice: Subject to any disclaimer, the term of this patent is extended or adjusted under 35 U.S.C. 154(b) by 0 days.

(21) Appl. No.: 15/517,805

(22) PCT Filed: Nov. 12, 2015

(86) PCT No.: PCT/US2015/060438
§ 371 (c)(1),
(2) Date: Apr. 7, 2017

(87) PCT Pub. No.: WO2016/077618
PCT Pub. Date: May 19, 2016

(65) Prior Publication Data
US 2018/0008721 A1 Jan. 11, 2018

Related U.S. Application Data

(60) Provisional application No. 62/078,752, filed on Nov. 12, 2014.

(51) Int. Cl.
| A61K 38/18 | (2006.01) |
| A61K 38/39 | (2006.01) |
| A61K 47/64 | (2017.01) |
| A61P 13/12 | (2006.01) |

(52) U.S. Cl.
CPC .......... *A61K 47/64* (2017.08); *A61K 38/1866* (2013.01); *A61K 38/39* (2013.01); *A61K 47/6435* (2017.08); *A61P 13/12* (2018.01)

(58) Field of Classification Search
None
See application file for complete search history.

(56) References Cited

U.S. PATENT DOCUMENTS

| 7,527,792 | B1 | 5/2009 | Temsamani et al. | |
| 2008/0032400 | A1 | 2/2008 | Dagher | |
| 2010/0022455 | A1* | 1/2010 | Chilkoti | A61K 38/26 514/18.8 |
| 2010/0022466 | A1* | 1/2010 | Raucher | A61K 41/0052 514/34 |
| 2010/0119529 | A1 | 5/2010 | Furgeson et al. | |
| 2011/0110866 | A1 | 5/2011 | Chilkoti et al. | |
| 2013/0172274 | A1 | 7/2013 | Chilkoti | |
| 2014/0323315 | A1 | 10/2014 | Bobrowicz et al. | |
| 2016/0297868 | A1* | 10/2016 | Bidwell, III | C07K 14/78 |

FOREIGN PATENT DOCUMENTS

| WO | WO97/10507 A1 | 3/1997 |
| WO | WO2014/014613 A3 | 1/2013 |

OTHER PUBLICATIONS

Wu et al. "Fabrication of Elastin-Like Polypeptide Nanoparticles for Drug Delivery by Electrospraying," Biomacromolecules 2009, 10, 19-24 (Year: 2009).*
Rousselle C, Clair P, Lefauconnier JM, et al. (2000) New advances in the transport of doxorubicin through the blood-brain barrier by a peptide vector-mediated strategy. Mol Pharmacol 57:679-86.
Vives E, Brodin P, Lebleu B (1997) A truncated HIV-1 Tat protein basic domain rapidly translocates through the plasma membrane and accumulates in the cell nucleus. J Biol Chem 272:16010-7.
Pasqualini R, Ruoslahti E (1996) Organ targeting in vivo using phage display peptide libraries. Nature 380:364-6. doi: 10.1038/380364a0.
Ritchie J, Green D, Chrysochou C, et al. (2014) High-risk clinical presentations in atherosclerotic renovascular disease: prognosis and response to renal artery revascularization. Am J Kidney Dis Off J Natl Kidney Found 63:186-197. doi: 10.1053/j.ajkd.2013.07.020.
Textor SC, Lerman LO (2014) Reality and renovascular disease: when does renal artery stenosis warrant revascularization? Am J Kidney Dis Off J Natl Kidney Found 63:175-177. doi: 10.1053/j.ajkd.2013.11.004.
Textor SC, Misra S, Oderich GS (2013) Percutaneous revascularization for ischemic nephropathy: the past, present, and future. Kidney Int 83:28-40. doi: 10.1038/ki.2012.363.
Cooper CJ, Murphy TP, Cutlip DE, et al. (2014) Stenting and medical therapy for atherosclerotic renal-artery stenosis. N Engl J Med 370:13-22. doi: 10.1056/NEJMoa1310753.
Chade AR, Kelsen S (2010) Renal microvascular disease determines the responses to revascularization in experimental renovascular disease. Circ Cardiovasc Interv 3:376-383. doi: 10.1161/CIRCINTERVENTIONS.110.951277.
Chade AR, Kelsen S (2012) Reversal of renal dysfunction by targeted administration of VEGF into the stenotic kidney: a novel potential therapeutic approach. Am J Physiol Ren Physiol 302:F1342-50. doi: 10.1152/ajprenal.00674.2011.

(Continued)

*Primary Examiner* — Christina Bradley
(74) *Attorney, Agent, or Firm* — Stites & Harbison PLLC; Richard S. Meyers, Jr.; Sean P. Ritchie

(57) ABSTRACT

A composition including an elastin-like polypeptide (ELP) coupled to a kidney targeting peptide and a therapeutic agent is provided. A method of delivering a therapeutic agent to a subject in need thereof comprising: administering to the subject an effective amount of a composition comprising: an elastin-like polypeptide (ELP), a kidney targeting agent coupled to the ELP and a targeting agent and/or a drug binding domain coupled to the ELP, wherein the ELP includes an amino acid sequence having at least about repeats of the amino acid sequence GVPGX (SEQ ID NO: 1), and wherein the composition enhances the deposition and retention of the therapeutic agent in the kidney relative to the non-conjugated therapeutic.

24 Claims, 14 Drawing Sheets
Specification includes a Sequence Listing.

(56) References Cited

OTHER PUBLICATIONS

Iliescu R, Fernandez SR, Kelsen S, et al. (2010) Role of renal microcirculation in experimental renovascular disease. Nephrol Dial Transplant Off Publ Eur Dial Transpl Assoc—Eur Ren Assoc 25:1079-1087. doi: 10.1093/ndt/gfp605.

Chade AR, Zhu X, Lavi R, et al. (2009) Endothelial progenitor cells restore renal function in chronic experimental renovascular disease. Circulation 119:547-557. doi: 10.1161/CIRCULATIONAHA. 108.788653.

Textor, et al.; Renal Artery Stenosis: Medical Versus Interventional Therapy; Curr Cardiol Rep (2013) 15:409; pp. 1-7.

Chade, et al.; Renal Therapeutic Angiogenesis Using a Bioengineered Polymer-Stabilized Vascular Endothelial Growth Factor Construct; J Am Soc Nephrol 27; 2015; pp. 1-12.

Stewart, et al.; Renoprotective effects of hepatocyte growth factor in the stenotic kidney; 2013; Am J Physiol Renal Physiol 304: F625-F633.

Bidwell, et al.; Thermally Targeted Delivery of a c-Myc Inhibitory Polypeptide Inhibits Tumor Progression and Extends Survival in a Rat Glioma Model; PLOS One; 2013; vol. 8; Issue 1; pp. 1-12.

Bidwell, et al.; A thermally targeted c-Myc inhibitory polypeptide inhibits breast tumor growth; Cancer Letters 319 (2012) 136-143.

Bidwell, et al.; A kidney-selective biopolymer for targeted drug delivery; 2017; Am J Physiol Renal Physiol 312: F54-F64.

George, et al., A polypeptide drug carrier for maternal delivery and prevention of fetal exposure; 2014; J Drug Target, Early Online: 1-13.

George, et al., Growth factor purification and delivery systems (PADS) for therapeutic angiogenesis; Vascular Cell (2015) 7:1; pp. 1-10.

Massodi, et al., Evaluation of Cell Penetrating Peptides Fused to Elastin-Like Polypeptide for Drug Delivery; Journal of Controlled Release; 108; 2005; pp. 396-408.

Dreher, et al., Evaluation of an elastin-like polypeptide-doxorubicin conjugate for cancer therapy; Journal of Controlled Release; 91; 2003; pp. 31-43.

Meyer, et al., Targeting a genetically engineered elastin-like polypeptide to solid tumors by local hyperthermia; Cancer Research; 61; pp. 1548-1554; Feb. 15, 2001.

\* cited by examiner

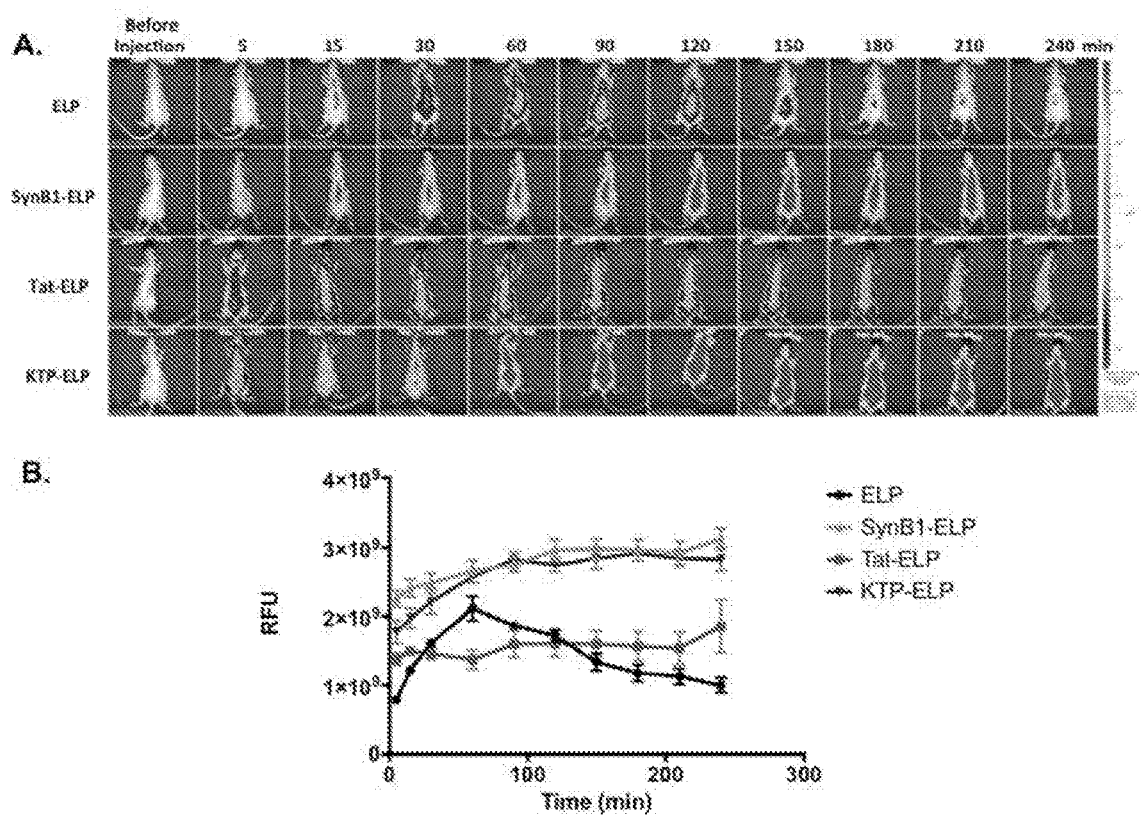

Figure 1. Biodistribution of kidney targeted ELPs in the rat. Rats were given fluorescently labeled ELP, Synb1-ELP, Tat-ELP, and KTP-ELP by intravenous injection. Whole-body fluorescence was determined by *in vivo* fluorescence imaging at various times after injection (A). The mean fluorescence intensity was determined at each time point and plotted to show tissue deposition and clearance (B). N = 3 rats per treatment group.

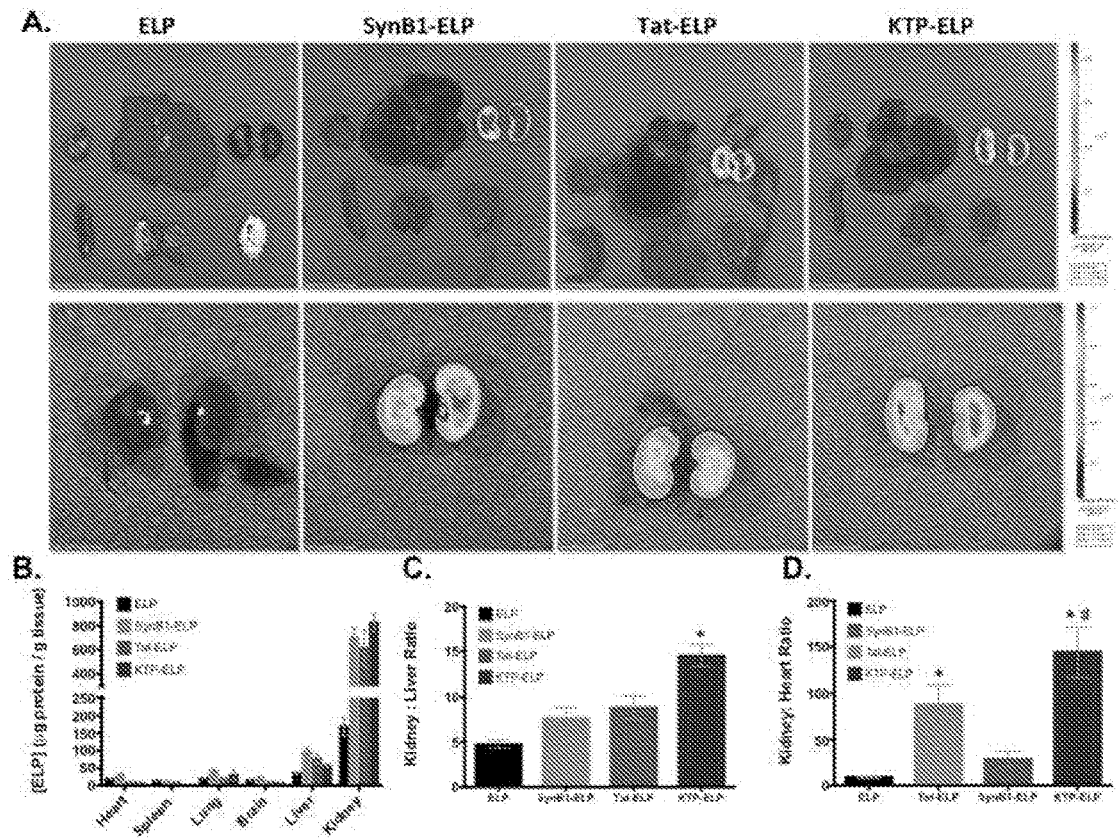

Figure 2. Enhancement of Kidney Specificity using Kidney Targeting Peptides. Rats were administered fluorescently labeled ELP, SynB1-ELP, Tat-ELP, or KTP-ELP, and organ biodistribution was determined by ex vivo fluorescence imaging (A.). Quantitative analysis showed that the highest accumulation of all peptides was in the kidney, and the targeting agents significantly increased kidney deposition (B.). KTP-ELP had the highest specificity for the kidney as assessed by kidney:liver and kidney:heart ratios (C. and D.).

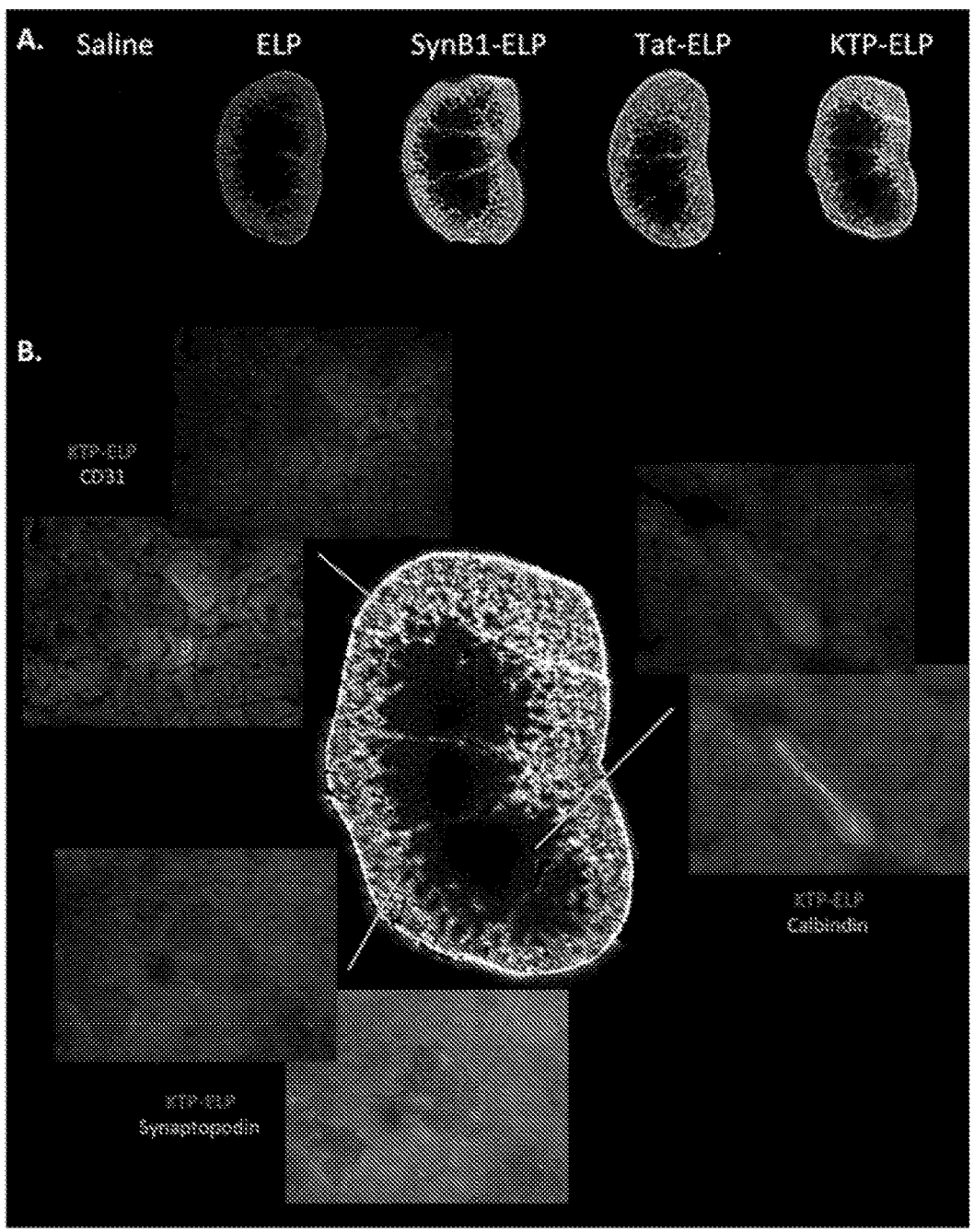

Figure 3. Intrarenal Distribution of Renally Targeted ELPs. Four hours after intravenous infusion of fluorescently labeled ELP, SynB1-ELP, Tat-ELP, or KTP-ELP, the kidneys were rapidly frozen and cut into 20 μm sections. A. Slides were scanned using a fluorescence slide scanner. Identical scan settings were used in order to directly compare the total kidney levels. B. Slides were stained with several vascular markers and imaged using a fluorescence microscope and 20x objective. Shown is the intrarenal distribution of KTP-ELP. Tat-ELP and SynB1-ELP had similar intrarenal distribution (not shown).

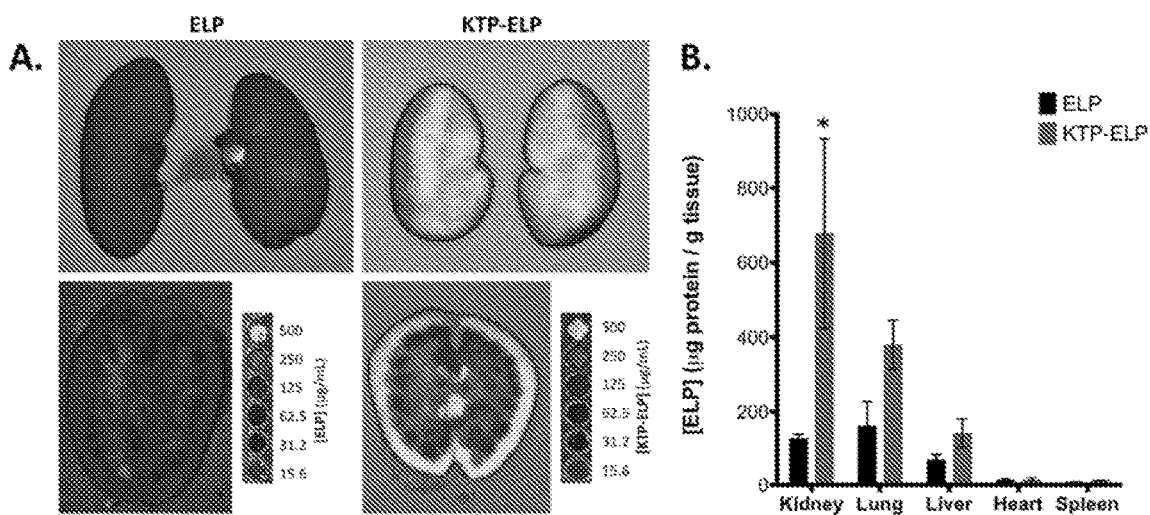
Figure 4. KTP enhances ELP deposition in the swine kidney after IV administration. Pigs (n=3 per agent) were given fluorescently labeled ELP or KTP-ELP by intravenous injection. Organ distribution was determined 4 h after injection by ex vivo whole organ fluorescence imaging (A) and quantified relative to standard curves of each agent (B).

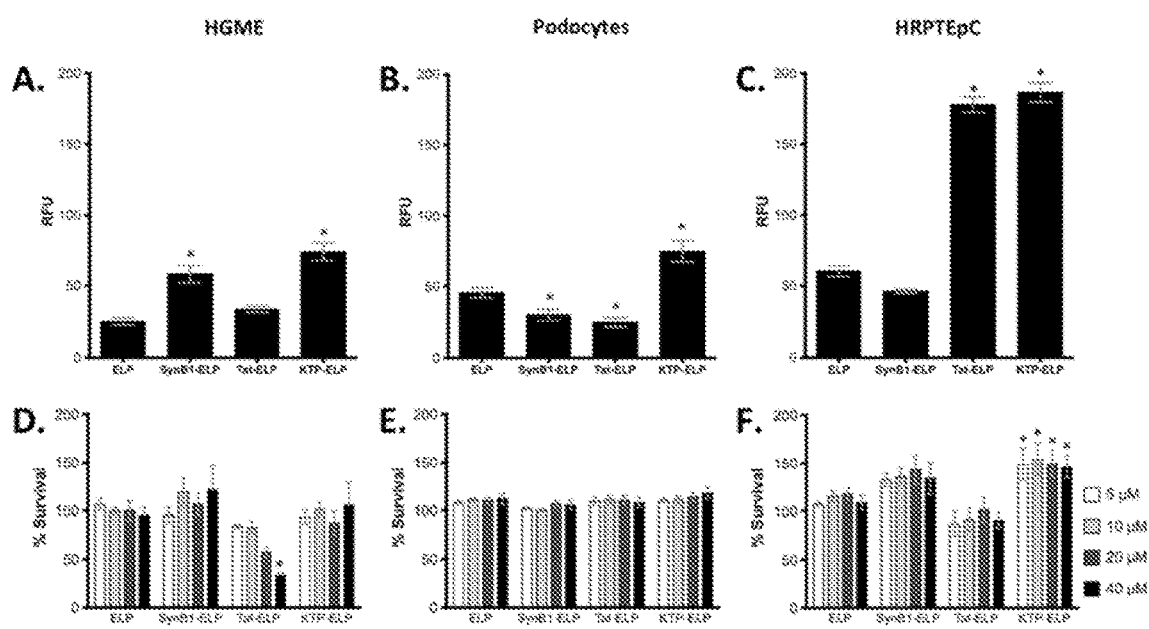

Figure 5. KTP-ELP enhances ELP binding to human renal cells. Cell binding (A-C) and cell survival (D-F) of SynB1-ELP, Tat-ELP, and KTP-ELP relative to ELP control were determined by flow cytometry and a cell viability assay, respectively, in primary human glomerular microvascular endothelial cells (A,D), primary human podocytes (B,E), and primary human proximal tubule epithelial cells (C,F).

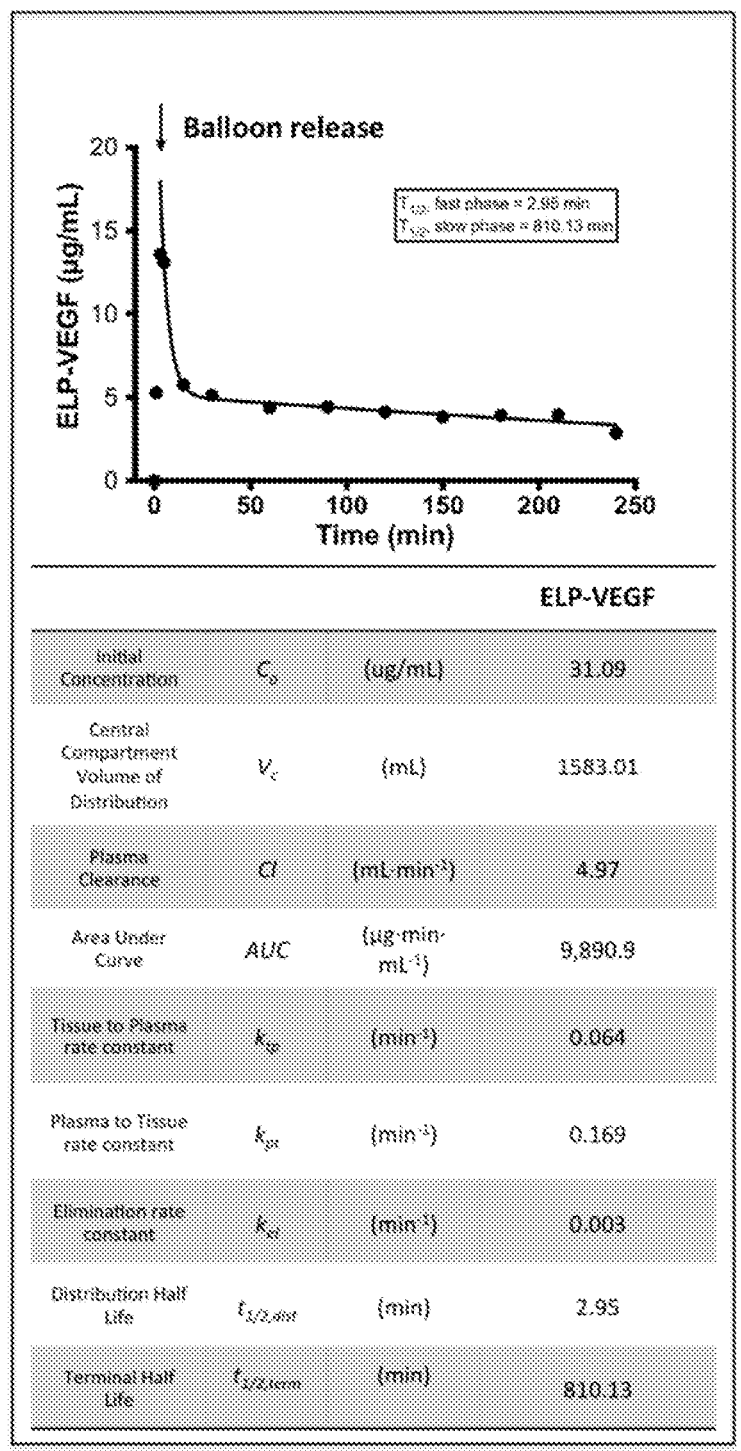

Figure 6. Pharmacokinetics of intrarenal ELP-VEGF in the Pig. Three pigs (average weight 49.2 kg) were given fluorescently labeled ELP-VEGF by direct intrarenal administration. A balloon was inflated o block blood flow into and out of the injected kidney for three minutes. The balloon was released, and plasma was sampled to determine ELP-VEGF levels. Plasma levels were determined by direct detection of fluorescence and fit to a two compartment pharmacokinetic model.

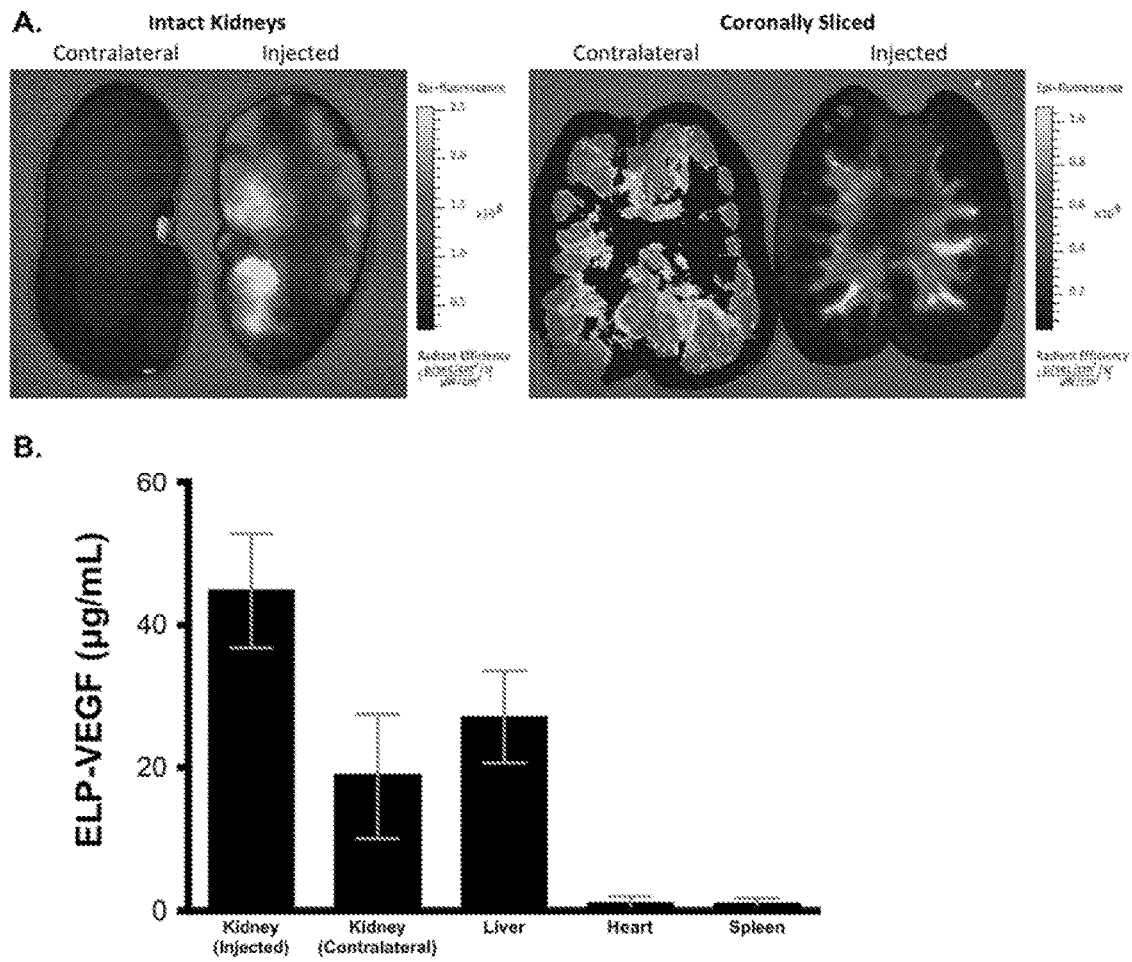
Figure 7. Biodistribution of intrarenal ELP-VEGF in the Pig. Three pigs were given fluorescently labeled ELP-VEGF by direct intrarenal administration. Organ distribution was determined 4 h after injection by *ex vivo* whole organ fluorescence imaging.

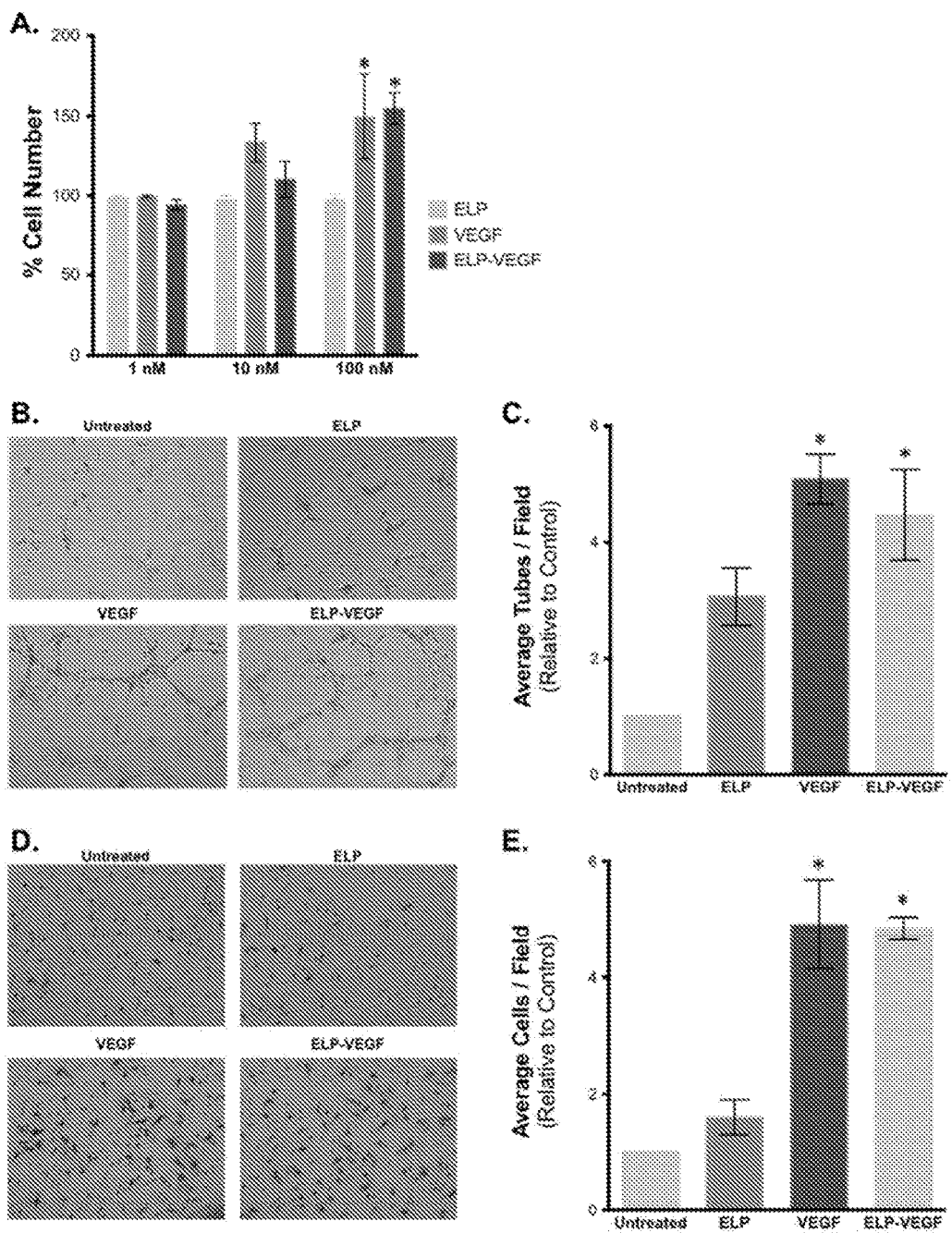

Figure 8. *In vitro* Activity of ELP-VEGF. A. Stimulation of HGME cell proliferation was determined by exposing HGME cells to ELP control, unconjugated VEGF, or ELP-VEGF for 72 h, and viable cells were detected using the MTS cell proliferation assay. B. and C. To determine if ELP-VEGF could stimulate tube formation in primary endothelial cells, HGME cells were plated on growth factor reduced Matrigel, and the media was supplemented with the indicated proteins. Tube formation was assessed after 5 h of exposure to the proteins. D. and E. To determine whether ELP-VEGF functions as a chemokine for primary endothelial cells, HGME cells were plated in the top well of Matrigel-coated Boyden chambers, and media in the bottom well was supplemented with the test proteins. Migrating cells were detected on the bottom surface of the membranes by crystal violet staining after 16 – 24 h of protein exposure. * Levels are significantly higher than untreated cells as assessed by a one-way ANOVA and post-hoc Bonferroni multiple comparison.

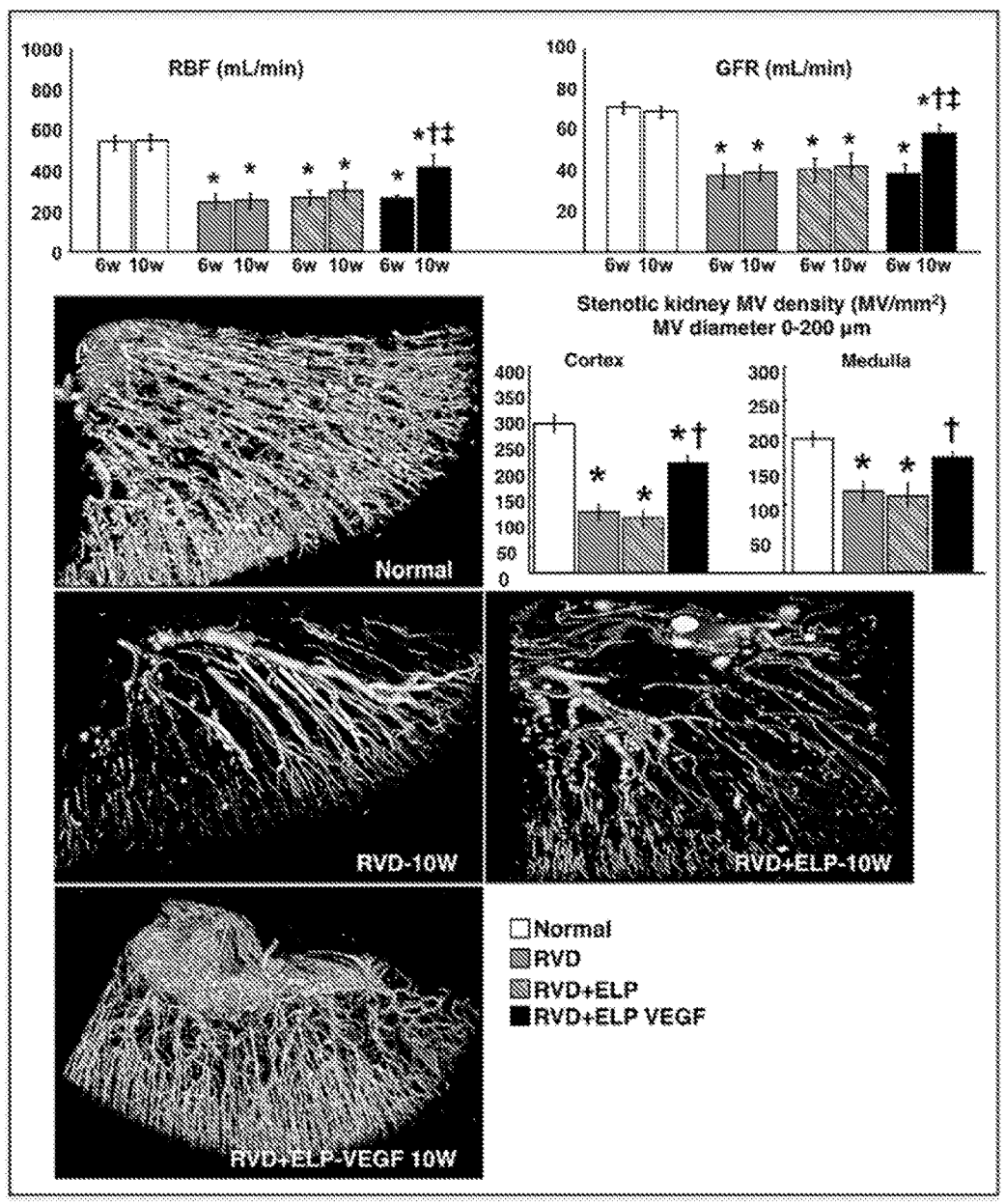

Figure 9A. Intra-renal administration of ELP-VEGF improved renal function, cortical and medullary vascular density in the stenotic kidney. Effect of intra-renal ELP-VEGF on renal function (top) and microvascular (MV) architecture (3D micro-CT reconstruction, bottom) and quantification in normal, renovascular disease (RVD), RVD+ELP, and RVD+ELP-VEGF treated kidneys. * $p<0.05$ vs. Normal; † $p<0.05$ vs. RVD/RVD+ELP; ‡ $p<0.05$ vs. 6 weeks.

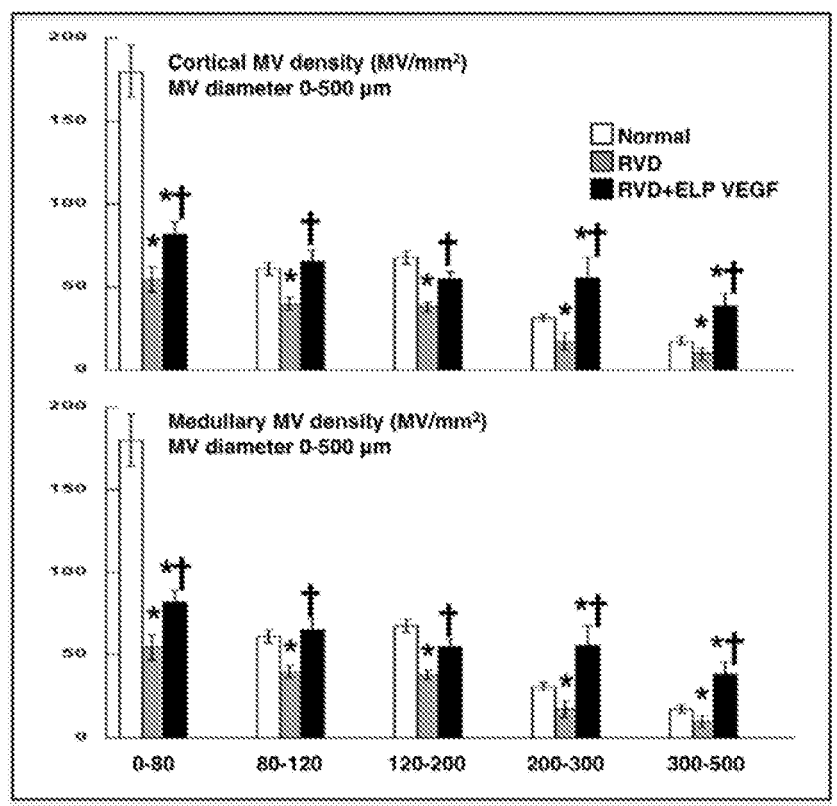
Figure 9B. Intra-renal administration of ELP-VEGF improved the vascular density of both small and larger MV diameters in the cortex and medulla of the stenotic kidney. Cortical and medullary quantification of microvascular (MV) density divided by MV diameter in normal, renovascular disease (RVD), and RVD+ELP-VEGF treated kidneys. * $p<0.05$ vs. Normal; † $p<0.05$ vs. RVD.

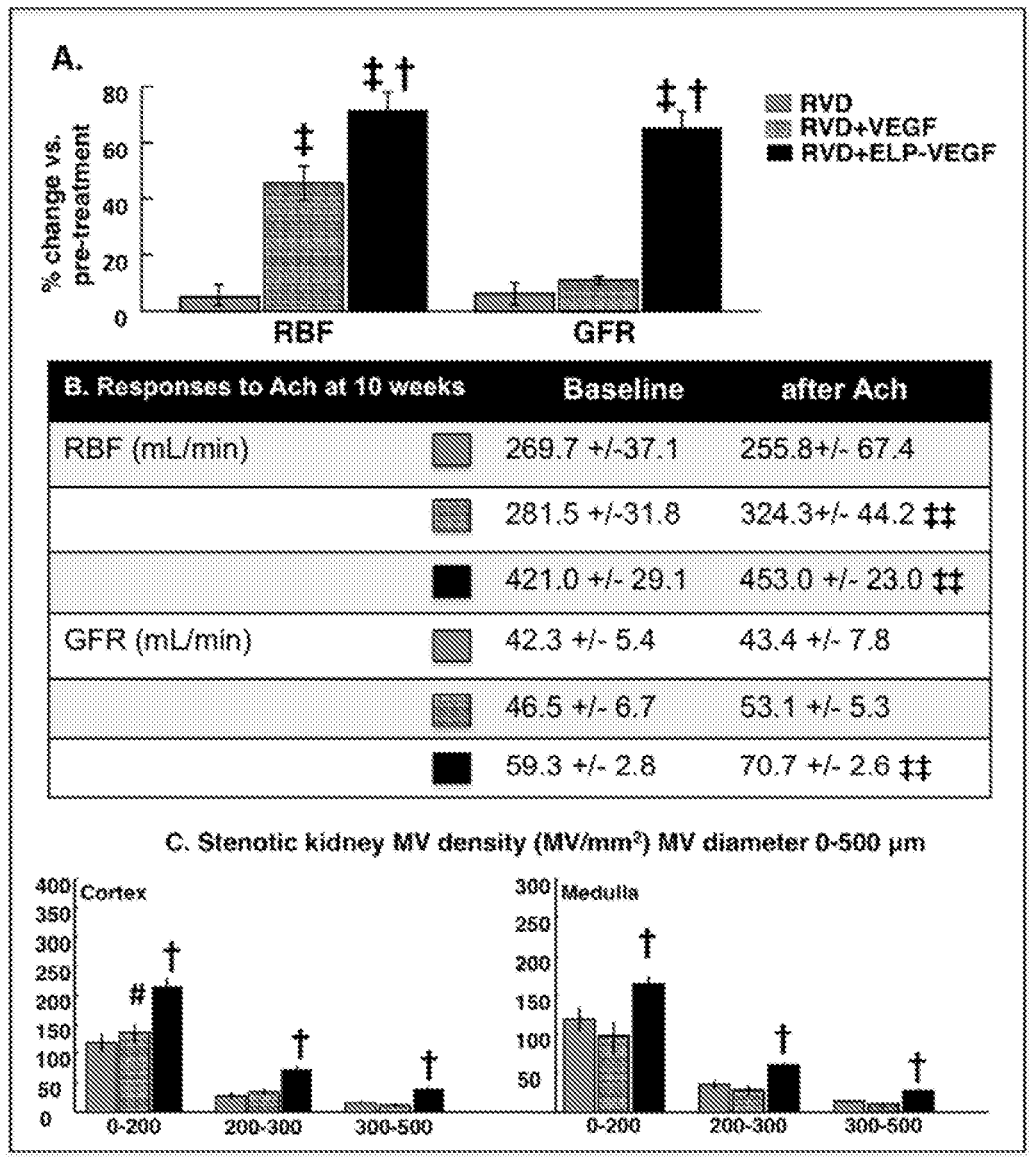

Figure 10: Intra-renal administration of ELP-VEGF improved stenotic kidney hemodynamics and microvascular (MV) rarefaction more efficiently than unbound VEGF. Comparisons between intra-renal unbound VEGF vs. ELP-VEGF therapy on: Top-basal stenotic kidney RBF and GFR, expressed as % change compared to pre-treatment values; Middle-RBF and GFR responses to intra-renal infusion of acetylcholine; Bottom-effects of the treatments on cortical and medullary MV density (3D micro-CT reconstruction, divided by MV diameter) in renovascular disease (RVD)+VEGF and RVD+ELP-VEGF treated kidneys. † $p<0.05$ vs. RVD/RVD+VEGF; ‡ $p<0.05$ vs. 6 weeks; ‡‡ $p<0.05$ vs. baseline; # $p=0.09$ vs. RVD.

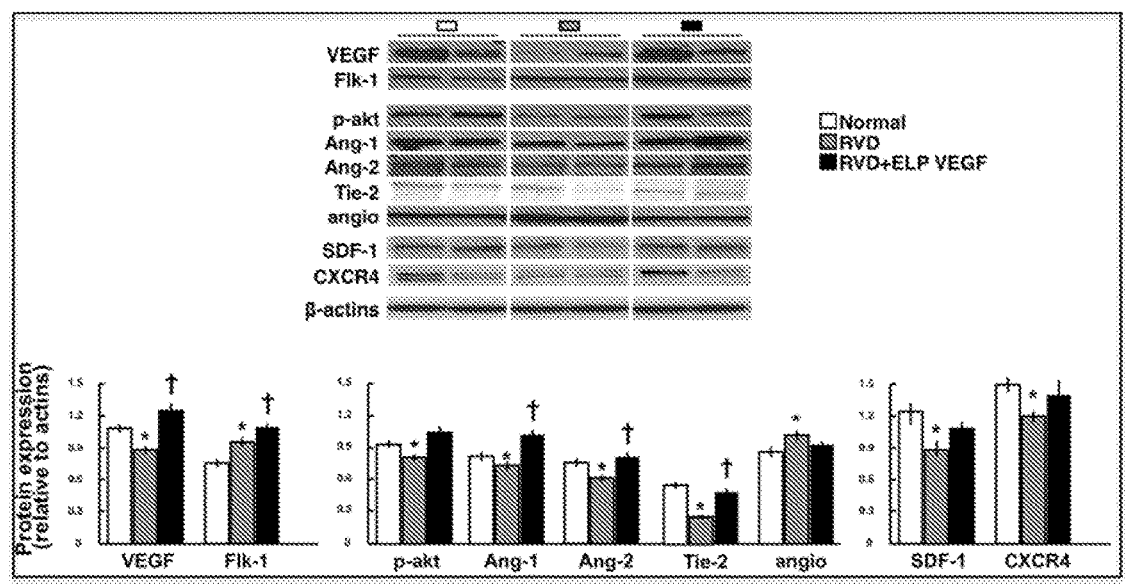

Figure 11. Intra-renal administration of ELP-VEGF improved the expression of angiogenic factors and promoters of mobilization and homing of progenitor cells in the stenotic kidney. Representative renal protein expression (top, 2 bands per group) of vascular endothelial growth factor (VEGF), its receptor Flk-1, phosphorylated (p)-akt, angiopoietin (Ang)-1 and -2, Tie-, angiostatin (angio), stromal-derived factor (SDF)-1 and its receptor CXCR4, and quantification (bottom) in normal, renovascular disease (RVD), and RVD+ELP-VEGF treated kidneys. * $p<0.05$ vs. Normal; † $p<0.05$ vs. RVD.

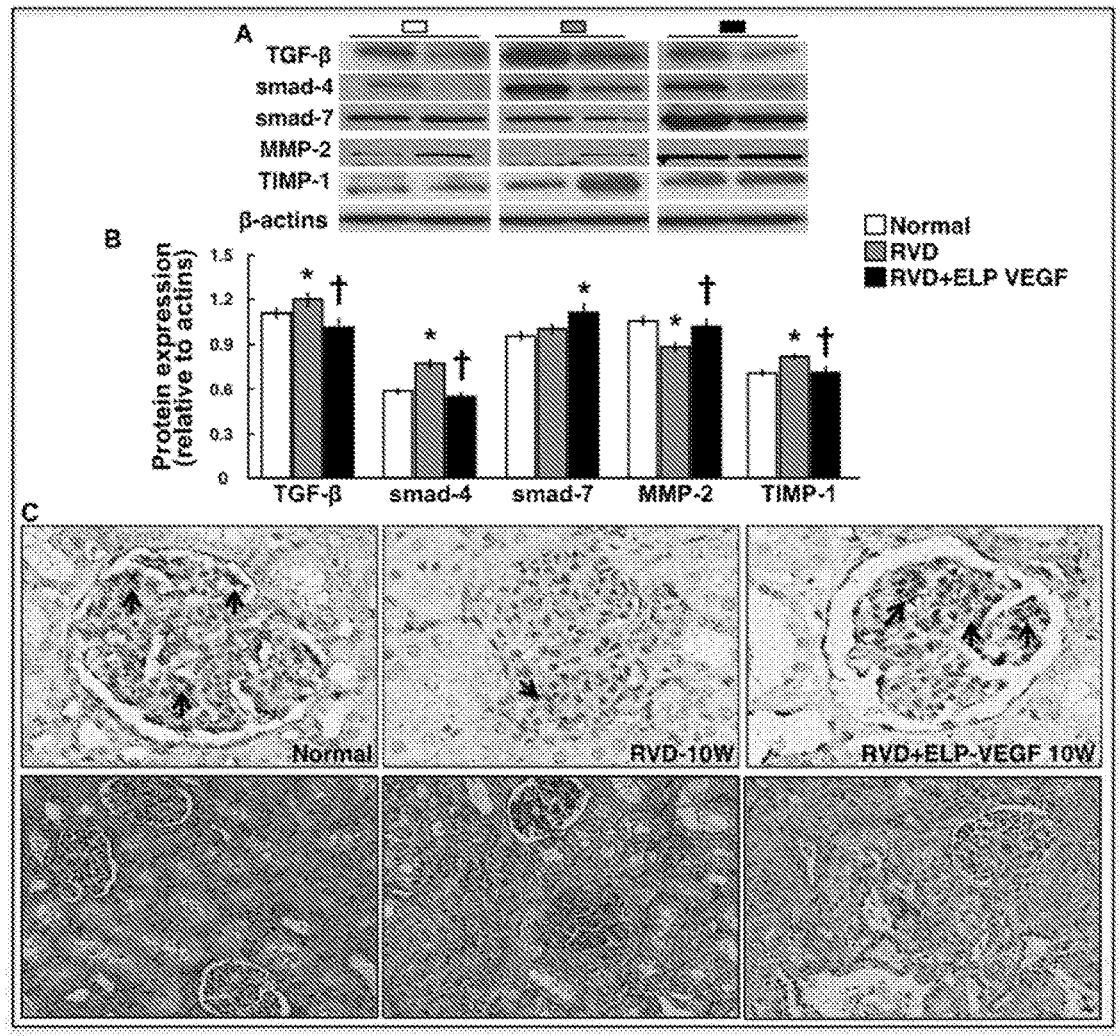

Figure 12. Intra-renal administration of ELP-VEGF reduced renal fibrogenic activity and attenuated podocyte damage and fibrosis in the stenotic kidney. Top: Representative renal protein expression (2 bands per group) and quantification of transforming growth factor (TGF)-β, smads-4 -7, matrix metalloproteinases (MMP)-2 and its inhibitor TIMP-1 in normal, renovascular disease (RVD), and RVD+ELP-VEGF treated kidneys. Middle: Representative pictures (from stenotic kidneys) of the glomeruli (x40), showed as examples to illustrate podocin immunoreactivity (black arrows). Bottom: Representative trichrome pictures (from stenotic kidneys) of the glomeruli and tubules, and tubule-interstitial regions (x20, showed as examples to illustrate renal damage). * $p<0.05$ vs. Normal; † $p<0.05$ vs. RVD.

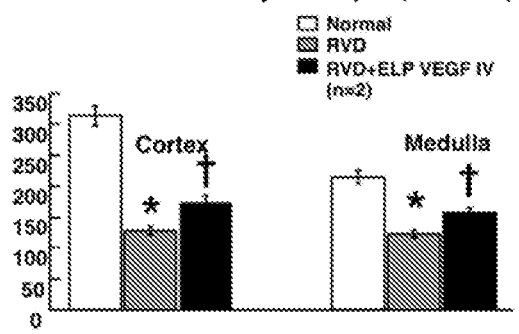
Figure 13. Effect of IV ELP-VEGF on Renal Function in RVD. A. Change in RBF and GFR after IV ELP-VEGF. B. Micro-CT quantification of renal MV density after IV ELP-VEGF. Intra-venous ELP-VEGF improved renal function and MV density of the stenotic kidney.
*$p<0.05$ vs. Normal;   † $p<0.05$ vs. RVD.

SEQUENCE LISTING

<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: ELP
<220> FEATURE:
<221> NAME/KEY: MISC_FEATURE
<222> LOCATION: (5)..(5)
<223> OTHER INFORMATION: Xaa can be any amino acid except Pro.

<400> SEQUENCE: 1

Gly Val Pro Gly Xaa
1               5

<210> SEQ ID NO 2
<211> LENGTH: 1600
<212> TYPE: PRT
<213> ORGANISM: Artificial Sequence
<220> FEATURE:
<223> OTHER INFORMATION: ELP
<220> FEATURE:
<221> NAME/KEY: MISC_FEATURE
<222> LOCATION: (1)..(1600)
<223> OTHER INFORMATION: The sequence is 20 repeating units of the
      sequence
      VPGVGVPGAGVPGGGVPGAGVPGGGVPGAGVPGGGVPGAGVPGGGVPGAGVPGGG
      VPGAGVPGGGVPGAG, i.e., n=20; however n can be an integer from 1
      to 20.

<400> SEQUENCE: 2

Val Pro Gly Val Gly Val Pro Gly Ala Gly Val Pro Gly Gly Gly Val
1               5                   10                  15

Pro Gly Ala Gly Val Pro Gly Gly Gly Val Pro Gly Ala Gly Val Pro
            20                  25                  30

Gly Gly Gly Val Pro Gly Ala Gly Val Pro Gly Gly Gly Val Pro Gly
        35                  40                  45

Ala Gly Val Pro Gly Gly Gly Val Pro Gly Ala Gly Val Pro Gly Gly
    50                  55                  60

Gly Val Pro Gly Ala Gly Val Pro Gly Gly Gly Val Pro Gly Ala Gly
65                  70                  75                  80

Val Pro Gly Val Gly Val Pro Gly Ala Gly Val Pro Gly Gly Gly Val
                85                  90                  95

Pro Gly Ala Gly Val Pro Gly Gly Gly Val Pro Gly Ala Gly Val Pro
            100                 105                 110

Gly Gly Gly Val Pro Gly Ala Gly Val Pro Gly Gly Gly Val Pro Gly
        115                 120                 125

Ala Gly Val Pro Gly Gly Gly Val Pro Gly Ala Gly Val Pro Gly Gly
    130                 135                 140

Gly Val Pro Gly Ala Gly Val Pro Gly Gly Gly Val Pro Gly Ala Gly
145                 150                 155                 160

Val Pro Gly Val Gly Val Pro Gly Ala Gly Val Pro Gly Gly Gly Val
                165                 170                 175

Pro Gly Ala Gly Val Pro Gly Gly Gly Val Pro Gly Ala Gly Val Pro
            180                 185                 190

Gly Gly Gly Val Pro Gly Ala Gly Val Pro Gly Gly Gly Val Pro Gly
        195                 200                 205

Ala Gly Val Pro Gly Gly Gly Val Pro Gly Ala Gly Val Pro Gly Gly
    210                 215                 220

-continued

Gly Val Pro Gly Ala Gly Val Pro Gly Gly Val Pro Gly Ala Gly
225                 230                 235                 240

Val Pro Gly Val Gly Val Pro Gly Ala Gly Val Pro Gly Gly Gly Val
                245                 250                 255

Pro Gly Ala Gly Val Pro Gly Gly Gly Val Pro Gly Ala Gly Val Pro
            260                 265                 270

Gly Gly Gly Val Pro Gly Ala Gly Val Pro Gly Gly Gly Val Pro Gly
        275                 280                 285

Ala Gly Val Pro Gly Gly Gly Val Pro Gly Ala Gly Val Pro Gly Gly
290                 295                 300

Gly Val Pro Gly Ala Gly Val Pro Gly Gly Gly Val Pro Gly Ala Gly
305                 310                 315                 320

Val Pro Gly Val Gly Val Pro Gly Ala Gly Val Pro Gly Gly Gly Val
                325                 330                 335

Pro Gly Ala Gly Val Pro Gly Gly Gly Val Pro Gly Ala Gly Val Pro
            340                 345                 350

Gly Gly Gly Val Pro Gly Ala Gly Val Pro Gly Gly Gly Val Pro Gly
        355                 360                 365

Ala Gly Val Pro Gly Gly Gly Val Pro Gly Ala Gly Val Pro Gly Gly
370                 375                 380

Gly Val Pro Gly Ala Gly Val Pro Gly Gly Gly Val Pro Gly Ala Gly
385                 390                 395                 400

Val Pro Gly Val Gly Val Pro Gly Ala Gly Val Pro Gly Gly Gly Val
                405                 410                 415

Pro Gly Ala Gly Val Pro Gly Gly Gly Val Pro Gly Ala Gly Val Pro
            420                 425                 430

Gly Gly Gly Val Pro Gly Ala Gly Val Pro Gly Gly Gly Val Pro Gly
        435                 440                 445

Ala Gly Val Pro Gly Gly Gly Val Pro Gly Ala Gly Val Pro Gly Gly
450                 455                 460

Gly Val Pro Gly Ala Gly Val Pro Gly Gly Gly Val Pro Gly Ala Gly
465                 470                 475                 480

Val Pro Gly Val Gly Val Pro Gly Ala Gly Val Pro Gly Gly Gly Val
                485                 490                 495

Pro Gly Ala Gly Val Pro Gly Gly Gly Val Pro Gly Ala Gly Val Pro
            500                 505                 510

Gly Gly Gly Val Pro Gly Ala Gly Val Pro Gly Gly Gly Val Pro Gly
        515                 520                 525

Ala Gly Val Pro Gly Gly Gly Val Pro Gly Ala Gly Val Pro Gly Gly
530                 535                 540

Gly Val Pro Gly Ala Gly Val Pro Gly Gly Gly Val Pro Gly Ala Gly
545                 550                 555                 560

Val Pro Gly Val Gly Val Pro Gly Ala Gly Val Pro Gly Gly Gly Val
                565                 570                 575

Pro Gly Ala Gly Val Pro Gly Gly Gly Val Pro Gly Ala Gly Val Pro
            580                 585                 590

Gly Gly Gly Val Pro Gly Ala Gly Val Pro Gly Gly Gly Val Pro Gly
        595                 600                 605

Ala Gly Val Pro Gly Gly Gly Val Pro Gly Ala Gly Val Pro Gly Gly
610                 615                 620

Gly Val Pro Gly Ala Gly Val Pro Gly Gly Gly Val Pro Gly Ala Gly
625                 630                 635                 640

Val Pro Gly Val Gly Val Pro Gly Ala Gly Val Pro Gly Gly Gly Val

```
                        645                 650                 655
Pro Gly Ala Gly Val Pro Gly Gly Val Pro Gly Ala Gly Val Pro
                660                 665                 670
Gly Gly Gly Val Pro Gly Ala Gly Val Pro Gly Gly Gly Val Pro Gly
            675                 680                 685
Ala Gly Val Pro Gly Gly Val Pro Gly Ala Gly Val Pro Gly Gly
        690                 695                 700
Gly Val Pro Gly Ala Gly Val Pro Gly Gly Gly Val Pro Gly Ala Gly
705                 710                 715                 720
Val Pro Gly Val Gly Val Pro Gly Ala Gly Val Pro Gly Gly Gly Val
                725                 730                 735
Pro Gly Ala Gly Val Pro Gly Gly Val Pro Gly Ala Gly Val Pro
                740                 745                 750
Gly Gly Gly Val Pro Gly Ala Gly Val Pro Gly Gly Gly Val Pro Gly
            755                 760                 765
Ala Gly Val Pro Gly Gly Val Pro Gly Ala Gly Val Pro Gly Gly
        770                 775                 780
Gly Val Pro Gly Ala Gly Val Pro Gly Gly Gly Val Pro Gly Ala Gly
785                 790                 795                 800
Val Pro Gly Val Gly Val Pro Gly Ala Gly Val Pro Gly Gly Gly Val
                805                 810                 815
Pro Gly Ala Gly Val Pro Gly Gly Val Pro Gly Ala Gly Val Pro
                820                 825                 830
Gly Gly Gly Val Pro Gly Ala Gly Val Pro Gly Gly Gly Val Pro Gly
            835                 840                 845
Ala Gly Val Pro Gly Gly Gly Val Pro Gly Ala Gly Val Pro Gly Gly
        850                 855                 860
Gly Val Pro Gly Ala Gly Val Pro Gly Gly Val Pro Gly Ala Gly
865                 870                 875                 880
Val Pro Gly Val Gly Val Pro Gly Ala Gly Val Pro Gly Gly Gly Val
                885                 890                 895
Pro Gly Ala Gly Val Pro Gly Gly Gly Val Pro Gly Ala Gly Val Pro
                900                 905                 910
Gly Gly Gly Val Pro Gly Ala Gly Val Pro Gly Gly Gly Val Pro Gly
            915                 920                 925
Ala Gly Val Pro Gly Gly Val Pro Gly Ala Gly Val Pro Gly Gly
        930                 935                 940
Gly Val Pro Gly Ala Gly Val Pro Gly Gly Gly Val Pro Gly Ala Gly
945                 950                 955                 960
Val Pro Gly Val Gly Val Pro Gly Ala Gly Val Pro Gly Gly Gly Val
                965                 970                 975
Pro Gly Ala Gly Val Pro Gly Gly Gly Val Pro Gly Ala Gly Val Pro
                980                 985                 990
Gly Gly Gly Val Pro Gly Ala Gly Val Pro Gly Gly Gly Val Pro Gly
            995                 1000                1005
Ala Gly Val Pro Gly Gly Gly Val Pro Gly Ala Gly Val Pro Gly
        1010                1015                1020
Gly Gly Val Pro Gly Ala Gly Val Pro Gly Gly Gly Val Pro Gly
        1025                1030                1035
Ala Gly Val Pro Gly Val Gly Val Pro Gly Ala Gly Val Pro Gly
        1040                1045                1050
Gly Gly Val Pro Gly Ala Gly Val Pro Gly Gly Gly Val Pro Gly
        1055                1060                1065
```

Ala Gly Val Pro Gly Gly Gly Val Pro Gly Ala Gly Val Pro Gly
1070                1075                1080

Gly Gly Val Pro Gly Ala Gly Val Pro Gly Gly Gly Val Pro Gly
1085                1090                1095

Ala Gly Val Pro Gly Gly Gly Val Pro Gly Ala Gly Val Pro Gly
1100                1105                1110

Gly Gly Val Pro Gly Ala Gly Val Pro Gly Val Gly Val Pro Gly
1115                1120                1125

Ala Gly Val Pro Gly Gly Gly Val Pro Gly Ala Gly Val Pro Gly
1130                1135                1140

Gly Gly Val Pro Gly Ala Gly Val Pro Gly Gly Gly Val Pro Gly
1145                1150                1155

Ala Gly Val Pro Gly Gly Gly Val Pro Gly Ala Gly Val Pro Gly
1160                1165                1170

Gly Gly Val Pro Gly Ala Gly Val Pro Gly Gly Gly Val Pro Gly
1175                1180                1185

Ala Gly Val Pro Gly Gly Gly Val Pro Gly Ala Gly Val Pro Gly
1190                1195                1200

Val Gly Val Pro Gly Ala Gly Val Pro Gly Gly Gly Val Pro Gly
1205                1210                1215

Ala Gly Val Pro Gly Gly Gly Val Pro Gly Ala Gly Val Pro Gly
1220                1225                1230

Gly Gly Val Pro Gly Ala Gly Val Pro Gly Gly Gly Val Pro Gly
1235                1240                1245

Ala Gly Val Pro Gly Gly Gly Val Pro Gly Ala Gly Val Pro Gly
1250                1255                1260

Gly Gly Val Pro Gly Ala Gly Val Pro Gly Gly Gly Val Pro Gly
1265                1270                1275

Ala Gly Val Pro Gly Val Gly Val Pro Gly Ala Gly Val Pro Gly
1280                1285                1290

Gly Gly Val Pro Gly Ala Gly Val Pro Gly Gly Gly Val Pro Gly
1295                1300                1305

Ala Gly Val Pro Gly Gly Gly Val Pro Gly Ala Gly Val Pro Gly
1310                1315                1320

Gly Gly Val Pro Gly Ala Gly Val Pro Gly Gly Gly Val Pro Gly
1325                1330                1335

Ala Gly Val Pro Gly Gly Gly Val Pro Gly Ala Gly Val Pro Gly
1340                1345                1350

Gly Gly Val Pro Gly Ala Gly Val Pro Gly Val Gly Val Pro Gly
1355                1360                1365

Ala Gly Val Pro Gly Gly Gly Val Pro Gly Ala Gly Val Pro Gly
1370                1375                1380

Gly Gly Val Pro Gly Ala Gly Val Pro Gly Gly Gly Val Pro Gly
1385                1390                1395

Ala Gly Val Pro Gly Gly Gly Val Pro Gly Ala Gly Val Pro Gly
1400                1405                1410

Gly Gly Val Pro Gly Ala Gly Val Pro Gly Gly Gly Val Pro Gly
1415                1420                1425

Ala Gly Val Pro Gly Gly Gly Val Pro Gly Ala Gly Val Pro Gly
1430                1435                1440

Val Gly Val Pro Gly Ala Gly Val Pro Gly Gly Gly Val Pro Gly
1445                1450                1455

```
Ala Gly Val Pro Gly Gly Gly Val Pro Gly Ala Gly Val Pro Gly
        1460                1465                1470

Gly Gly Val Pro Gly Ala Gly Val Pro Gly Gly Gly Val Pro Gly
        1475                1480                1485

Ala Gly Val Pro Gly Gly Gly Val Pro Gly Ala Gly Val Pro Gly
        1490                1495                1500

Gly Gly Val Pro Gly Ala Gly Val Pro Gly Gly Gly Val Pro Gly
        1505                1510                1515

Ala Gly Val Pro Gly Val Gly Val Pro Gly Ala Gly Val Pro Gly
        1520                1525                1530

Gly Gly Val Pro Gly Ala Gly Val Pro Gly Gly Gly Val Pro Gly
        1535                1540                1545

Ala Gly Val Pro Gly Gly Gly Val Pro Gly Ala Gly Val Pro Gly
        1550                1555                1560

Gly Gly Val Pro Gly Ala Gly Val Pro Gly Gly Gly Val Pro Gly
        1565                1570                1575

Ala Gly Val Pro Gly Gly Gly Val Pro Gly Ala Gly Val Pro Gly
        1580                1585                1590

Gly Gly Val Pro Gly Ala Gly
        1595                1600

<210> SEQ ID NO 3
<211> LENGTH: 1600
<212> TYPE: PRT
<213> ORGANISM: Artificial Sequence
<220> FEATURE:
<223> OTHER INFORMATION: ELP
<220> FEATURE:
<221> NAME/KEY: MISC_FEATURE
<222> LOCATION: (1)..(1600)
<223> OTHER INFORMATION: The sequence includes 320 repeating units of
      the amino acid sequence GVPGG, i.e., n=320; however, this unit
      can be repeated such that n is an integer from 5 to 320.

<400> SEQUENCE: 3

Gly Val Pro Gly Gly Gly Val Pro Gly Gly Gly Val Pro Gly Gly
1               5                   10                  15

Val Pro Gly Gly Gly Val Pro Gly Gly Gly Val Pro Gly Gly Gly Val
            20                  25                  30

Pro Gly Gly Gly Val Pro Gly Gly Gly Val Pro Gly Gly Gly Val Pro
        35                  40                  45

Gly Gly Gly Val Pro Gly Gly Gly Val Pro Gly Gly Gly Val Pro Gly
    50                  55                  60

Gly Gly Val Pro Gly Gly Gly Val Pro Gly Gly Gly Val Pro Gly Gly
65                  70                  75                  80

Gly Val Pro Gly Gly Gly Val Pro Gly Gly Gly Val Pro Gly Gly Gly
                85                  90                  95

Val Pro Gly Gly Gly Val Pro Gly Gly Gly Val Pro Gly Gly Gly Val
            100                 105                 110

Pro Gly Gly Gly Val Pro Gly Gly Gly Val Pro Gly Gly Gly Val Pro
        115                 120                 125

Gly Gly Gly Val Pro Gly Gly Gly Val Pro Gly Gly Gly Val Pro Gly
    130                 135                 140

Gly Gly Val Pro Gly Gly Gly Val Pro Gly Gly Gly Val Pro Gly Gly
145                 150                 155                 160

Gly Val Pro Gly Gly Gly Val Pro Gly Gly Gly Val Pro Gly Gly Gly
                165                 170                 175
```

```
Val Pro Gly Gly Gly Val Pro Gly Gly Gly Val
        180                 185                 190

Pro Gly Gly Gly Val Pro Gly Gly Gly Val Pro Gly Gly Gly Val Pro
            195                 200                 205

Gly Gly Gly Val Pro Gly Gly Gly Val Pro Gly Gly Gly Val Pro Gly
        210                 215                 220

Gly Gly Val Pro Gly Gly Gly Val Pro Gly Gly Gly Val Pro Gly Gly
225                 230                 235                 240

Gly Val Pro Gly Gly Gly Val Pro Gly Gly Gly Val Pro Gly Gly Gly
            245                 250                 255

Val Pro Gly Gly Gly Val Pro Gly Gly Gly Val Pro Gly Gly Gly Val
        260                 265                 270

Pro Gly Gly Gly Val Pro Gly Gly Gly Val Pro Gly Gly Gly Val Pro
            275                 280                 285

Gly Gly Gly Val Pro Gly Gly Gly Val Pro Gly Gly Gly Val Pro Gly
        290                 295                 300

Gly Gly Val Pro Gly Gly Gly Val Pro Gly Gly Gly Val Pro Gly Gly
305                 310                 315                 320

Gly Val Pro Gly Gly Gly Val Pro Gly Gly Gly Val Pro Gly Gly Gly
            325                 330                 335

Val Pro Gly Gly Gly Val Pro Gly Gly Gly Val Pro Gly Gly Gly Val
        340                 345                 350

Pro Gly Gly Gly Val Pro Gly Gly Gly Val Pro Gly Gly Gly Val Pro
            355                 360                 365

Gly Gly Gly Val Pro Gly Gly Gly Val Pro Gly Gly Gly Val Pro Gly
        370                 375                 380

Gly Gly Val Pro Gly Gly Gly Val Pro Gly Gly Gly Val Pro Gly Gly
385                 390                 395                 400

Gly Val Pro Gly Gly Gly Val Pro Gly Gly Gly Val Pro Gly Gly Gly
            405                 410                 415

Val Pro Gly Gly Gly Val Pro Gly Gly Gly Val Pro Gly Gly Gly Val
        420                 425                 430

Pro Gly Gly Gly Val Pro Gly Gly Gly Val Pro Gly Gly Gly Val Pro
            435                 440                 445

Gly Gly Gly Val Pro Gly Gly Gly Val Pro Gly Gly Gly Val Pro Gly
        450                 455                 460

Gly Gly Val Pro Gly Gly Gly Val Pro Gly Gly Gly Val Pro Gly Gly
465                 470                 475                 480

Gly Val Pro Gly Gly Gly Val Pro Gly Gly Gly Val Pro Gly Gly Gly
            485                 490                 495

Val Pro Gly Gly Gly Val Pro Gly Gly Gly Val Pro Gly Gly Gly Val
        500                 505                 510

Pro Gly Gly Gly Val Pro Gly Gly Gly Val Pro Gly Gly Gly Val Pro
            515                 520                 525

Gly Gly Gly Val Pro Gly Gly Gly Val Pro Gly Gly Gly Val Pro Gly
        530                 535                 540

Gly Gly Val Pro Gly Gly Gly Val Pro Gly Gly Gly Val Pro Gly Gly
545                 550                 555                 560

Gly Val Pro Gly Gly Gly Val Pro Gly Gly Gly Val Pro Gly Gly Gly
            565                 570                 575

Val Pro Gly Gly Gly Val Pro Gly Gly Gly Val Pro Gly Gly Gly Val
        580                 585                 590

Pro Gly Gly Gly Val Pro Gly Gly Gly Val Pro Gly Gly Gly Val Pro
```

```
                595                 600                 605
Gly Gly Gly Val Pro Gly Gly Val Pro Gly Gly Val Pro Gly
            610                 615                 620
Gly Gly Val Pro Gly Gly Val Pro Gly Gly Val Pro Gly Gly
625                 630                 635                 640
Gly Val Pro Gly Gly Val Pro Gly Gly Val Pro Gly Gly Gly
                645                 650                 655
Val Pro Gly Gly Val Pro Gly Gly Val Pro Gly Gly Gly Val
            660                 665                 670
Pro Gly Gly Gly Val Pro Gly Gly Gly Val Pro Gly Gly Val Pro
        675                 680                 685
Gly Gly Gly Val Pro Gly Gly Gly Val Pro Gly Gly Val Pro Gly
        690                 695                 700
Gly Gly Val Pro Gly Gly Gly Val Pro Gly Gly Val Pro Gly Gly
705                 710                 715                 720
Gly Val Pro Gly Gly Val Pro Gly Gly Val Pro Gly Gly Gly
                725                 730                 735
Val Pro Gly Gly Gly Val Pro Gly Gly Gly Val Pro Gly Gly Val
            740                 745                 750
Pro Gly Gly Gly Val Pro Gly Gly Gly Val Pro Gly Gly Val Pro
        755                 760                 765
Gly Gly Gly Val Pro Gly Gly Val Pro Gly Gly Val Pro Gly
770                 775                 780
Gly Gly Val Pro Gly Gly Val Pro Gly Gly Val Pro Gly Gly
785                 790                 795                 800
Gly Val Pro Gly Gly Val Pro Gly Gly Val Pro Gly Gly Gly
            805                 810                 815
Val Pro Gly Gly Gly Val Pro Gly Gly Gly Val Pro Gly Gly Val
            820                 825                 830
Pro Gly Gly Gly Val Pro Gly Gly Gly Val Pro Gly Gly Val Pro
        835                 840                 845
Gly Gly Gly Val Pro Gly Gly Gly Val Pro Gly Gly Val Pro Gly
        850                 855                 860
Gly Gly Val Pro Gly Gly Val Pro Gly Gly Val Pro Gly Gly
865                 870                 875                 880
Gly Val Pro Gly Gly Val Pro Gly Gly Val Pro Gly Gly Gly
                885                 890                 895
Val Pro Gly Gly Val Pro Gly Gly Val Pro Gly Gly Gly Val
            900                 905                 910
Pro Gly Gly Gly Val Pro Gly Gly Gly Val Pro Gly Gly Val Pro
        915                 920                 925
Gly Gly Gly Val Pro Gly Gly Gly Val Pro Gly Gly Val Pro Gly
        930                 935                 940
Gly Gly Val Pro Gly Gly Val Pro Gly Gly Val Pro Gly Gly
945                 950                 955                 960
Gly Val Pro Gly Gly Val Pro Gly Gly Val Pro Gly Gly Gly
                965                 970                 975
Val Pro Gly Gly Val Pro Gly Gly Val Pro Gly Gly Gly Val
            980                 985                 990
Pro Gly Gly Gly Val Pro Gly Gly  Gly Val Pro Gly Gly  Gly Val Pro
        995                 1000                 1005
Gly Gly  Gly Val Pro Gly Gly  Gly Val Pro Gly Gly  Gly Val Pro
    1010                 1015                 1020
```

-continued

Gly Gly Gly Val Pro Gly Gly Gly Val Pro Gly Gly Gly Val Pro
    1025                1030                1035

Gly Gly Gly Val Pro Gly Gly Gly Val Pro Gly Gly Gly Val Pro
    1040                1045                1050

Gly Gly Gly Val Pro Gly Gly Gly Val Pro Gly Gly Gly Val Pro
    1055                1060                1065

Gly Gly Gly Val Pro Gly Gly Gly Val Pro Gly Gly Gly Val Pro
    1070                1075                1080

Gly Gly Gly Val Pro Gly Gly Gly Val Pro Gly Gly Gly Val Pro
    1085                1090                1095

Gly Gly Gly Val Pro Gly Gly Gly Val Pro Gly Gly Gly Val Pro
    1100                1105                1110

Gly Gly Gly Val Pro Gly Gly Gly Val Pro Gly Gly Gly Val Pro
    1115                1120                1125

Gly Gly Gly Val Pro Gly Gly Gly Val Pro Gly Gly Gly Val Pro
    1130                1135                1140

Gly Gly Gly Val Pro Gly Gly Gly Val Pro Gly Gly Gly Val Pro
    1145                1150                1155

Gly Gly Gly Val Pro Gly Gly Gly Val Pro Gly Gly Gly Val Pro
    1160                1165                1170

Gly Gly Gly Val Pro Gly Gly Gly Val Pro Gly Gly Gly Val Pro
    1175                1180                1185

Gly Gly Gly Val Pro Gly Gly Gly Val Pro Gly Gly Gly Val Pro
    1190                1195                1200

Gly Gly Gly Val Pro Gly Gly Gly Val Pro Gly Gly Gly Val Pro
    1205                1210                1215

Gly Gly Gly Val Pro Gly Gly Gly Val Pro Gly Gly Gly Val Pro
    1220                1225                1230

Gly Gly Gly Val Pro Gly Gly Gly Val Pro Gly Gly Gly Val Pro
    1235                1240                1245

Gly Gly Gly Val Pro Gly Gly Gly Val Pro Gly Gly Gly Val Pro
    1250                1255                1260

Gly Gly Gly Val Pro Gly Gly Gly Val Pro Gly Gly Gly Val Pro
    1265                1270                1275

Gly Gly Gly Val Pro Gly Gly Gly Val Pro Gly Gly Gly Val Pro
    1280                1285                1290

Gly Gly Gly Val Pro Gly Gly Gly Val Pro Gly Gly Gly Val Pro
    1295                1300                1305

Gly Gly Gly Val Pro Gly Gly Gly Val Pro Gly Gly Gly Val Pro
    1310                1315                1320

Gly Gly Gly Val Pro Gly Gly Gly Val Pro Gly Gly Gly Val Pro
    1325                1330                1335

Gly Gly Gly Val Pro Gly Gly Gly Val Pro Gly Gly Gly Val Pro
    1340                1345                1350

Gly Gly Gly Val Pro Gly Gly Gly Val Pro Gly Gly Gly Val Pro
    1355                1360                1365

Gly Gly Gly Val Pro Gly Gly Gly Val Pro Gly Gly Gly Val Pro
    1370                1375                1380

Gly Gly Gly Val Pro Gly Gly Gly Val Pro Gly Gly Gly Val Pro
    1385                1390                1395

Gly Gly Gly Val Pro Gly Gly Gly Val Pro Gly Gly Gly Val Pro
    1400                1405                1410

-continued

```
Gly Gly  Gly Val Pro Gly Gly  Gly Val Pro Gly Gly  Gly Val Pro
    1415             1420             1425

Gly Gly  Gly Val Pro Gly Gly  Gly Val Pro Gly Gly  Gly Val Pro
    1430             1435             1440

Gly Gly  Gly Val Pro Gly Gly  Gly Val Pro Gly Gly  Gly Val Pro
    1445             1450             1455

Gly Gly  Gly Val Pro Gly Gly  Gly Val Pro Gly Gly  Gly Val Pro
    1460             1465             1470

Gly Gly  Gly Val Pro Gly Gly  Gly Val Pro Gly Gly  Gly Val Pro
    1475             1480             1485

Gly Gly  Gly Val Pro Gly Gly  Gly Val Pro Gly Gly  Gly Val Pro
    1490             1495             1500

Gly Gly  Gly Val Pro Gly Gly  Gly Val Pro Gly Gly  Gly Val Pro
    1505             1510             1515

Gly Gly  Gly Val Pro Gly Gly  Gly Val Pro Gly Gly  Gly Val Pro
    1520             1525             1530

Gly Gly  Gly Val Pro Gly Gly  Gly Val Pro Gly Gly  Gly Val Pro
    1535             1540             1545

Gly Gly  Gly Val Pro Gly Gly  Gly Val Pro Gly Gly  Gly Val Pro
    1550             1555             1560

Gly Gly  Gly Val Pro Gly Gly  Gly Val Pro Gly Gly  Gly Val Pro
    1565             1570             1575

Gly Gly  Gly Val Pro Gly Gly  Gly Val Pro Gly Gly  Gly Val Pro
    1580             1585             1590

Gly Gly  Gly Val Pro Gly Gly
    1595             1600

<210> SEQ ID NO 4
<211> LENGTH: 1600
<212> TYPE: PRT
<213> ORGANISM: Artificial Sequence
<220> FEATURE:
<223> OTHER INFORMATION: ELP
<220> FEATURE:
<221> NAME/KEY: MISC_FEATURE
<222> LOCATION: (1)..(1600)
<223> OTHER INFORMATION: The sequence includes 40 repeating units of
      the amino acid sequence VPGVGVPGAGVPGGGVPGAGVPGGGVPGAGVPGGGVPGAG,
      i.e., n=40; however, this unit can be repeated such that n is an
      integer from 1 to 40.

<400> SEQUENCE: 4

Val Pro Gly Val Gly Val Pro Gly Ala Gly Val Pro Gly Gly Val
1               5                  10                  15

Pro Gly Ala Gly Val Pro Gly Gly Gly Val Pro Gly Ala Gly Val Pro
                20                  25                  30

Gly Gly Gly Val Pro Gly Ala Gly Val Pro Gly Val Gly Val Pro Gly
            35                  40                  45

Ala Gly Val Pro Gly Gly Val Pro Gly Ala Gly Val Pro Gly Gly
        50                  55                  60

Gly Val Pro Gly Ala Gly Val Pro Gly Gly Gly Val Pro Gly Ala Gly
65                  70                  75                  80

Val Pro Gly Val Gly Val Pro Gly Ala Gly Val Pro Gly Gly Gly Val
                85                  90                  95

Pro Gly Ala Gly Val Pro Gly Gly Gly Val Pro Gly Ala Gly Val Pro
                100                 105                 110

Gly Gly Gly Val Pro Gly Ala Gly Val Pro Gly Val Gly Val Pro Gly
            115                 120                 125
```

```
Ala Gly Val Pro Gly Gly Val Pro Gly Ala Val Pro Gly Gly
        130                 135                 140

Gly Val Pro Gly Ala Gly Val Pro Gly Gly Val Pro Gly Ala Gly
145                 150                 155                 160

Val Pro Gly Val Gly Val Pro Gly Ala Gly Val Pro Gly Gly Val
                165                 170                 175

Pro Gly Ala Gly Val Pro Gly Gly Val Pro Gly Ala Gly Val Pro
            180                 185                 190

Gly Gly Gly Val Pro Gly Ala Gly Val Pro Gly Val Gly Val Pro Gly
        195                 200                 205

Ala Gly Val Pro Gly Gly Val Pro Gly Ala Gly Val Pro Gly Gly
        210                 215                 220

Gly Val Pro Gly Ala Gly Val Pro Gly Gly Val Pro Gly Ala Gly
225                 230                 235                 240

Val Pro Gly Val Gly Val Pro Gly Ala Gly Val Pro Gly Gly Val
                245                 250                 255

Pro Gly Ala Gly Val Pro Gly Gly Val Pro Gly Ala Gly Val Pro
            260                 265                 270

Gly Gly Gly Val Pro Gly Ala Gly Val Pro Gly Val Gly Val Pro Gly
        275                 280                 285

Ala Gly Val Pro Gly Gly Val Pro Gly Ala Gly Val Pro Gly Gly
        290                 295                 300

Gly Val Pro Gly Ala Gly Val Pro Gly Gly Val Pro Gly Ala Gly
305                 310                 315                 320

Val Pro Gly Val Gly Val Pro Gly Ala Gly Val Pro Gly Gly Val
                325                 330                 335

Pro Gly Ala Gly Val Pro Gly Gly Val Pro Gly Ala Gly Val Pro
            340                 345                 350

Gly Gly Gly Val Pro Gly Ala Gly Val Pro Gly Val Gly Val Pro Gly
        355                 360                 365

Ala Gly Val Pro Gly Gly Val Pro Gly Ala Gly Val Pro Gly Gly
        370                 375                 380

Gly Val Pro Gly Ala Gly Val Pro Gly Gly Val Pro Gly Ala Gly
385                 390                 395                 400

Val Pro Gly Val Gly Val Pro Gly Ala Gly Val Pro Gly Gly Val
                405                 410                 415

Pro Gly Ala Gly Val Pro Gly Gly Val Pro Gly Ala Gly Val Pro
            420                 425                 430

Gly Gly Gly Val Pro Gly Ala Gly Val Pro Gly Val Gly Val Pro Gly
        435                 440                 445

Ala Gly Val Pro Gly Gly Val Pro Gly Ala Gly Val Pro Gly Gly
        450                 455                 460

Gly Val Pro Gly Ala Gly Val Pro Gly Gly Val Pro Gly Ala Gly
465                 470                 475                 480

Val Pro Gly Val Gly Val Pro Gly Ala Gly Val Pro Gly Gly Val
                485                 490                 495

Pro Gly Ala Gly Val Pro Gly Gly Val Pro Gly Ala Gly Val Pro
            500                 505                 510

Gly Gly Gly Val Pro Gly Ala Gly Val Pro Gly Val Gly Val Pro Gly
        515                 520                 525

Ala Gly Val Pro Gly Gly Val Pro Gly Ala Gly Val Pro Gly Gly
        530                 535                 540
```

```
Gly Val Pro Gly Ala Gly Val Pro Gly Gly Gly Val Pro Gly Ala Gly
545                 550                 555                 560
Val Pro Gly Val Gly Val Pro Gly Ala Gly Val Pro Gly Gly Gly Val
                565                 570                 575
Pro Gly Ala Gly Val Pro Gly Gly Gly Val Pro Gly Ala Gly Val Pro
            580                 585                 590
Gly Gly Gly Val Pro Gly Ala Gly Val Pro Gly Val Gly Val Pro Gly
        595                 600                 605
Ala Gly Val Pro Gly Gly Gly Val Pro Gly Ala Gly Val Pro Gly Gly
    610                 615                 620
Gly Val Pro Gly Ala Gly Val Pro Gly Gly Gly Val Pro Gly Ala Gly
625                 630                 635                 640
Val Pro Gly Val Gly Val Pro Gly Ala Gly Val Pro Gly Gly Gly Val
                645                 650                 655
Pro Gly Ala Gly Val Pro Gly Gly Gly Val Pro Gly Ala Gly Val Pro
            660                 665                 670
Gly Gly Gly Val Pro Gly Ala Gly Val Pro Gly Val Gly Val Pro Gly
        675                 680                 685
Ala Gly Val Pro Gly Gly Gly Val Pro Gly Ala Gly Val Pro Gly Gly
    690                 695                 700
Gly Val Pro Gly Ala Gly Val Pro Gly Gly Gly Val Pro Gly Ala Gly
705                 710                 715                 720
Val Pro Gly Val Gly Val Pro Gly Ala Gly Val Pro Gly Gly Gly Val
                725                 730                 735
Pro Gly Ala Gly Val Pro Gly Gly Gly Val Pro Gly Ala Gly Val Pro
            740                 745                 750
Gly Gly Gly Val Pro Gly Ala Gly Val Pro Gly Val Gly Val Pro Gly
        755                 760                 765
Ala Gly Val Pro Gly Gly Gly Val Pro Gly Ala Gly Val Pro Gly Gly
    770                 775                 780
Gly Val Pro Gly Ala Gly Val Pro Gly Gly Gly Val Pro Gly Ala Gly
785                 790                 795                 800
Val Pro Gly Val Gly Val Pro Gly Ala Gly Val Pro Gly Gly Gly Val
                805                 810                 815
Pro Gly Ala Gly Val Pro Gly Gly Gly Val Pro Gly Ala Gly Val Pro
            820                 825                 830
Gly Gly Gly Val Pro Gly Ala Gly Val Pro Gly Val Gly Val Pro Gly
        835                 840                 845
Ala Gly Val Pro Gly Gly Gly Val Pro Gly Ala Gly Val Pro Gly Gly
    850                 855                 860
Gly Val Pro Gly Ala Gly Val Pro Gly Gly Gly Val Pro Gly Ala Gly
865                 870                 875                 880
Val Pro Gly Val Gly Val Pro Gly Ala Gly Val Pro Gly Gly Gly Val
                885                 890                 895
Pro Gly Ala Gly Val Pro Gly Gly Gly Val Pro Gly Ala Gly Val Pro
            900                 905                 910
Gly Gly Gly Val Pro Gly Ala Gly Val Pro Gly Val Gly Val Pro Gly
        915                 920                 925
Ala Gly Val Pro Gly Gly Gly Val Pro Gly Ala Gly Val Pro Gly Gly
    930                 935                 940
Gly Val Pro Gly Ala Gly Val Pro Gly Gly Gly Val Pro Gly Ala Gly
945                 950                 955                 960
Val Pro Gly Val Gly Val Pro Gly Ala Gly Val Pro Gly Gly Gly Val
```

965                 970                 975
Pro Gly Ala Gly Val Pro Gly Gly Val Pro Gly Ala Gly Val Pro
            980                 985                 990
Gly Gly Val Pro Gly Ala Gly Val Pro Gly Val Gly Val Pro Gly
        995                1000                1005
Ala Gly Val Pro Gly Gly Val Pro Gly Ala Gly Val Pro Gly
    1010                1015                1020
Gly Gly Val Pro Gly Ala Gly Val Pro Gly Gly Gly Val Pro Gly
    1025                1030                1035
Ala Gly Val Pro Gly Val Gly Val Pro Gly Ala Gly Val Pro Gly
    1040                1045                1050
Gly Gly Val Pro Gly Ala Gly Val Pro Gly Gly Gly Val Pro Gly
    1055                1060                1065
Ala Gly Val Pro Gly Gly Gly Val Pro Gly Ala Gly Val Pro Gly
    1070                1075                1080
Val Gly Val Pro Gly Ala Gly Val Pro Gly Gly Gly Val Pro Gly
    1085                1090                1095
Ala Gly Val Pro Gly Gly Gly Val Pro Gly Ala Gly Val Pro Gly
    1100                1105                1110
Gly Gly Val Pro Gly Ala Gly Val Pro Gly Val Gly Val Pro Gly
    1115                1120                1125
Ala Gly Val Pro Gly Gly Gly Val Pro Gly Ala Gly Val Pro Gly
    1130                1135                1140
Gly Gly Val Pro Gly Ala Gly Val Pro Gly Gly Gly Val Pro Gly
    1145                1150                1155
Ala Gly Val Pro Gly Val Gly Val Pro Gly Ala Gly Val Pro Gly
    1160                1165                1170
Gly Gly Val Pro Gly Ala Gly Val Pro Gly Gly Gly Val Pro Gly
    1175                1180                1185
Ala Gly Val Pro Gly Gly Gly Val Pro Gly Ala Gly Val Pro Gly
    1190                1195                1200
Val Gly Val Pro Gly Ala Gly Val Pro Gly Gly Gly Val Pro Gly
    1205                1210                1215
Ala Gly Val Pro Gly Gly Gly Val Pro Gly Ala Gly Val Pro Gly
    1220                1225                1230
Gly Gly Val Pro Gly Ala Gly Val Pro Gly Val Gly Val Pro Gly
    1235                1240                1245
Ala Gly Val Pro Gly Gly Gly Val Pro Gly Ala Gly Val Pro Gly
    1250                1255                1260
Gly Gly Val Pro Gly Ala Gly Val Pro Gly Gly Gly Val Pro Gly
    1265                1270                1275
Ala Gly Val Pro Gly Val Gly Val Pro Gly Ala Gly Val Pro Gly
    1280                1285                1290
Gly Gly Val Pro Gly Ala Gly Val Pro Gly Gly Gly Val Pro Gly
    1295                1300                1305
Ala Gly Val Pro Gly Gly Gly Val Pro Gly Ala Gly Val Pro Gly
    1310                1315                1320
Val Gly Val Pro Gly Ala Gly Val Pro Gly Gly Gly Val Pro Gly
    1325                1330                1335
Ala Gly Val Pro Gly Gly Gly Val Pro Gly Ala Gly Val Pro Gly
    1340                1345                1350
Gly Gly Val Pro Gly Ala Gly Val Pro Gly Val Gly Val Pro Gly
    1355                1360                1365

Ala Gly Val Pro Gly Gly Gly Val Pro Gly Ala Gly Val Pro Gly
    1370                1375                1380

Gly Gly Val Pro Gly Ala Gly Val Pro Gly Gly Gly Val Pro Gly
    1385                1390                1395

Ala Gly Val Pro Gly Val Gly Val Pro Gly Ala Gly Val Pro Gly
    1400                1405                1410

Gly Gly Val Pro Gly Ala Gly Val Pro Gly Gly Gly Val Pro Gly
    1415                1420                1425

Ala Gly Val Pro Gly Gly Gly Val Pro Gly Ala Gly Val Pro Gly
    1430                1435                1440

Val Gly Val Pro Gly Ala Gly Val Pro Gly Gly Gly Val Pro Gly
    1445                1450                1455

Ala Gly Val Pro Gly Gly Gly Val Pro Gly Ala Gly Val Pro Gly
    1460                1465                1470

Gly Gly Val Pro Gly Ala Gly Val Pro Gly Val Gly Val Pro Gly
    1475                1480                1485

Ala Gly Val Pro Gly Gly Gly Val Pro Gly Ala Gly Val Pro Gly
    1490                1495                1500

Gly Gly Val Pro Gly Ala Gly Val Pro Gly Gly Gly Val Pro Gly
    1505                1510                1515

Ala Gly Val Pro Gly Val Gly Val Pro Gly Ala Gly Val Pro Gly
    1520                1525                1530

Gly Gly Val Pro Gly Ala Gly Val Pro Gly Gly Gly Val Pro Gly
    1535                1540                1545

Ala Gly Val Pro Gly Gly Gly Val Pro Gly Ala Gly Val Pro Gly
    1550                1555                1560

Val Gly Val Pro Gly Ala Gly Val Pro Gly Gly Gly Val Pro Gly
    1565                1570                1575

Ala Gly Val Pro Gly Gly Gly Val Pro Gly Ala Gly Val Pro Gly
    1580                1585                1590

Gly Gly Val Pro Gly Ala Gly
    1595                1600

<210> SEQ ID NO 5
<211> LENGTH: 7
<212> TYPE: PRT
<213> ORGANISM: Artificial Sequence
<220> FEATURE:
<223> OTHER INFORMATION: Kidney Targeting Peptide

<400> SEQUENCE: 5

Cys Leu Pro Val Ala Ser Cys
1               5

<210> SEQ ID NO 6
<211> LENGTH: 7
<212> TYPE: PRT
<213> ORGANISM: Artificial Sequence
<220> FEATURE:
<223> OTHER INFORMATION: Kidney Targeting Peptide

<400> SEQUENCE: 6

Cys Gly Ala Arg Glu Met Cys
1               5

<210> SEQ ID NO 7
<211> LENGTH: 11
<212> TYPE: PRT

<213> ORGANISM: Artificial Sequence
<220> FEATURE:
<223> OTHER INFORMATION: Tat Peptide

<400> SEQUENCE: 7

Tyr Gly Arg Lys Lys Arg Arg Gln Arg Arg
1               5                   10

<210> SEQ ID NO 8
<211> LENGTH: 18
<212> TYPE: PRT
<213> ORGANISM: Artificial Sequence
<220> FEATURE:
<223> OTHER INFORMATION: SynB1 Peptide

<400> SEQUENCE: 8

Arg Gly Gly Arg Leu Ser Tyr Ser Arg Arg Phe Ser Thr Ser Thr
1               5                   10                  15

Gly Arg

<210> SEQ ID NO 9
<211> LENGTH: 90
<212> TYPE: PRT
<213> ORGANISM: Artificial Sequence
<220> FEATURE:
<223> OTHER INFORMATION: Drug Binding Domain
<220> FEATURE:
<221> NAME/KEY: MISC_FEATURE
<222> LOCATION: (1)..(90)
<223> OTHER INFORMATION: The sequence includes 10 repeating units of
      the amino acid sequence GGCGGCGGC, i.e., n=10; however this unit
      can be repeated such that n is an integer from 1 to 10.

<400> SEQUENCE: 9

Gly Gly Cys Gly Gly Cys Gly Gly Cys Gly Gly Cys Gly Gly Cys Gly
1               5                   10                  15

Gly Cys Gly Gly Cys Gly Gly Cys Gly Gly Cys Gly Gly Cys Gly Gly
                20                  25                  30

Cys Gly Gly Cys Gly Gly Cys Gly Gly Cys Gly Gly Cys Gly Gly Cys
            35                  40                  45

Gly Gly Cys Gly Gly Cys Gly Gly Cys Gly Gly Cys Gly Gly Cys Gly
        50                  55                  60

Gly Cys Gly Gly Cys Gly Gly Cys Gly Gly Cys Gly Gly Cys Gly Gly
65                  70                  75                  80

Cys Gly Gly Cys Gly Gly Cys Gly Gly Cys
                85                  90

<210> SEQ ID NO 10
<211> LENGTH: 60
<212> TYPE: PRT
<213> ORGANISM: Artificial Sequence
<220> FEATURE:
<223> OTHER INFORMATION: Drug Binding Domain
<220> FEATURE:
<221> NAME/KEY: MISC_FEATURE
<222> LOCATION: (1)..(60)
<223> OTHER INFORMATION: The sequence includes 10 repeating units of
      the amino acid sequence GCGCGC, i.e., n=10; however this unit can
      be repeated such that n is an integer from 1 to 10.

<400> SEQUENCE: 10

Gly Cys Gly Cys Gly Cys Gly Cys Gly Cys Gly Cys Gly Cys Gly Cys
1               5                   10                  15

Gly Cys Gly Cys Gly Cys Gly Cys Gly Cys Gly Cys Gly Cys Gly Cys
                20                  25                  30

```
Gly Cys Gly Cys Gly Cys Gly Cys Gly Cys Gly Cys Gly Cys
            35                  40                  45

Gly Cys Gly Cys Gly Cys Gly Cys Gly Cys Gly Cys
        50                  55                  60

<210> SEQ ID NO 11
<211> LENGTH: 90
<212> TYPE: PRT
<213> ORGANISM: Artificial Sequence
<220> FEATURE:
<223> OTHER INFORMATION: Drug Binding Domain
<220> FEATURE:
<221> NAME/KEY: MISC_FEATURE
<222> LOCATION: (1)..(90)
<223> OTHER INFORMATION: The sequence includes 10 repeating units of
      the amino acid sequence GGKGGKGGK, i.e., n=10; however, this unit
      can be repeated such that n is an integer from 1 to 10.

<400> SEQUENCE: 11

Gly Gly Lys Gly Gly Lys Gly Gly Lys Gly Gly Lys Gly Gly Lys Gly
1               5                   10                  15

Gly Lys Gly Gly Lys Gly Gly Lys Gly Gly Lys Gly Gly Lys Gly Gly
            20                  25                  30

Lys Gly Gly Lys Gly Gly Lys Gly Gly Lys Gly Gly Lys Gly Gly Lys
            35                  40                  45

Gly Gly Lys Gly Gly Lys Gly Gly Lys Gly Gly Lys Gly Gly Lys Gly
        50                  55                  60

Gly Lys Gly Gly Lys Gly Gly Lys Gly Gly Lys Gly Gly Lys Gly Gly
65                  70                  75                  80

Lys Gly Gly Lys Gly Gly Lys Gly Gly Lys
                85                  90

<210> SEQ ID NO 12
<211> LENGTH: 60
<212> TYPE: PRT
<213> ORGANISM: Artificial Sequence
<220> FEATURE:
<223> OTHER INFORMATION: Drug Binding Domain
<220> FEATURE:
<221> NAME/KEY: MISC_FEATURE
<222> LOCATION: (1)..(60)
<223> OTHER INFORMATION: The sequence includes 10 repeating units of
      the amino acid sequence GKGKGK, i.e., n=10; however, this unit can
      be repeated such that n is an integer from 1 to 10.

<400> SEQUENCE: 12

Gly Lys Gly Lys Gly Lys Gly Lys Gly Lys Gly Lys Gly Lys Gly Lys
1               5                   10                  15

Gly Lys Gly Lys Gly Lys Gly Lys Gly Lys Gly Lys Gly Lys Gly Lys
            20                  25                  30

Gly Lys Gly Lys Gly Lys Gly Lys Gly Lys Gly Lys Gly Lys Gly Lys
            35                  40                  45

Gly Lys Gly Lys Gly Lys Gly Lys Gly Lys Gly Lys
        50                  55                  60
```

KIDNEY-TARGETED DRUG DELIVERY SYSTEMS

RELATED APPLICATIONS

This application claims priority from International Patent Application No. PCT/US2015/060438, filed Nov. 12, 2015, which claims priority from U.S. Provisional Application Ser. No. 62/078,752 filed Nov. 12, 2014, the entire disclosures of which are incorporated herein by this reference.

STATEMENT OF GOVERNMENT SUPPORT

This presently-disclosed subject matter was made with government support under grant number R01HL095638 and R01HL121527 awarded by the National Institutes of Health. The government has certain rights in it.

TECHNICAL FIELD

The presently-disclosed subject matter generally relates to a composition and method for therapeutic agent delivery of kidney diseases treatment. More particularly, the presently-disclosed subject matter relates to a composition comprising an elastin-like polypeptide (ELP) coupled to kidney targeting peptides and a therapeutic agent or agents, and a method of delivering the composition to a subject in need thereof.

INTRODUCTION

The kidney plays a critical role in sodium/water balance, maintenance of blood pressure, and removal of waste products from the circulatory system. Damage or disease to the kidneys can have very serious consequences including the often irreversible need to place patients on hemodialysis for the remainder of their life. Therefore, the kidney is an important drug target, and therapies that can prevent loss of kidney function or even restore function in damaged kidneys would have great clinical value.

Chronic kidney disease (CKD) is a progressive disorder affecting almost 14% of the general adult population, and this disease has shown a continuous growth over the past 2 decades. Patients with CKD have higher rates of hospitalization, greater mortality, shorter life expectancy, and their healthcare costs are up to 5 times more expensive than non-CKD patients. Thus, treatments to slow, halt, or reverse the progression of CKD could have a significant impact. Chronic renal vascular disease (RVD), often associated with renal artery stenosis, can deteriorate renal function and lead to CKD and end-stage renal disease. Despite the availability of treatments for RVD including drugs and renal angioplasty, renal function does not improve or even deteriorates in over half of the patients undergoing these treatments. This evidence shows that treatments available are still largely ineffective and highlights a pressing need for novel therapeutic strategies for the growing population of patients suffering from RVD.

BRIEF DESCRIPTION OF THE DRAWINGS

FIG. 1 includes a series of images and a graph depicting the biodistribution of kidney targeted ELPs in the rat. Rats were given fluorescently labeled ELP, Synb1-ELP, Tat-ELP, and KTP-ELP by intravenous injection. Whole-body fluorescence was determined by in vivo fluorescence imaging at various times after injection (A). The mean fluorescence intensity was determined at each time point and plotted to show tissue deposition and clearance (B). N=3 rats per treatment group.

FIG. 2 includes a series of images and graphs demonstrating the enhancement of kidney specificity using Kidney Targeting Peptides. Rats were administered fluorescently labeled ELP, SynB1-ELP, Tat-ELP, or KTP-ELP, and organ biodistribution was determined by ex vivo fluorescence imaging (A.). Quantitative analysis showed that the highest accumulation of all peptides was in the kidney, and the targeting agents significantly increased kidney deposition (B.). KTP-ELP had the highest specificity for the kidney as assessed by kidney:liver and kidney:heart ratios (C. and D.).

FIG. 3 includes a series of slide scans and micrographs depicting the intrarenal distribution of renally targeted ELPs. Four hours after intravenous infusion of fluorescently labeled ELP, SynB1-ELP, Tat-ELP, or KTP-ELP, the kidneys were rapidly frozen and cut into 20 μm sections. A. Slides were scanned using a fluorescence slide scanner. Identical scan settings were used in order to directly compare the total kidney levels. B. Slides were stained with several vascular markers and imaged using a fluorescence microscope and 20× objective. Shown is the intrarenal distribution of KTP-ELP. Tat-ELP and SynB1-ELP had similar intrarenal distribution (not shown).

FIG. 4 includes fluorescence photographs and a bar graph showing that KTP enhances ELP deposition in the swine kidney after IV administration. Pigs (n=3 per agent) were given fluorescently labeled ELP or KTP-ELP by intravenous injection. Organ distribution was determined 4 h after injection by er vivo whole organ fluorescence imaging (A) and quantified relative to standard curves of each agent (B).

FIG. 5 includes a series of bar graphs demonstrating that KTP-ELP enhances ELP binding to human renal cells. Cell binding (A-C) and cell survival (D-F) of SynB1-ELP, Tat-ELP, and KTP-ELP relative to ELP control were determined by flow cytometry and a cell viability assay, respectively, in primary human glomerular microvascular endothelial cells (A,D), primary human podocytes (B,E), and primary human proximal tubule epithelial cells (C,F).

FIG. 6 contains a scatter plot and tabular data depicting the pharmacokinetics of intrarenal ELP-VEGF in the Pig. Three pigs (average weight 49.2 kg) were given fluorescently labeled ELP-VEGF by direct intrarenal administration. A balloon was inflated o block blood flow into and out of the injected kidney for three minutes. The balloon was released, and plasma was sampled to determine ELP-VEGF levels. Plasma levels were determined by direct detection of fluorescence and fit to a two compartment pharmacokinetic model.

FIG. 7 includes a series of images and a graph depicting the intrarenal biodistribution of ELP-VEGF in the Pig. Three pigs were given fluorescently labeled ELP-VEGF by direct intrarenal administration. Organ distribution was determined 4 h after injection by ex vivo whole organ fluorescence imaging.

FIG. 8 includes a series of bar graphs and images demonstrating that ELP-VEGF maintains its pro-angiogenic activity. A. Stimulation of HGME cell proliferation was determined by exposing HGME cells to ELP control, unconjugated VEGF, or ELP-VEGF for 72 h, and viable cells were detected using the MTS cell proliferation assay. B. and C. To determine if ELP-VEGF could stimulate tube formation in primary endothelial cells, HGME cells were plated on growth factor reduced Matrigel, and the media was supplemented with the indicated proteins. Tube formation was assessed after 5 h of exposure to the proteins. D. and E. To determine whether ELP-VEGF functions as a chemokine for primary endothelial cells, HGME cells were plated in the top well of Matrigel-coated Boyden chambers, and media in the bottom well was supplemented with the test proteins. Migrating cells were detected on the bottom surface of the membranes by crystal violet staining after 16-24 h of protein exposure. *Levels are significantly higher than untreated cells as assessed by a one-way ANOVA and post-hoc Bonferroni multiple comparison.

FIG. 9 includes a series of graphs and images demonstrating the effect of intrarenal ELP-VEGF on renal function in RVD. FIG. 9A shows that intra-renal administration of ELP-VEGF improved renal function, cortical and medullary vascular density in the stenotic kidney. Effect of intra-renal ELP-VEGF on renal function (top) and microvascular (MV) architecture (3D micro-CT reconstruction, bottom) and quantification in normal, renovascular disease (RVD), RVD+ELP, and RVD+ELP-VEGF treated kidneys. *$p<0.05$ vs. Normal; †$p<0.05$ vs. RVD/RVD+ELP; ‡$p<0.05$ vs. 6 weeks. FIG. 9B shows that intra-renal administration of ELP-VEGF improved the vascular density of both small and larger MV diameters in the cortex and medulla of the stenotic kidney. Cortical and medullary quantification of microvascular (MV) density divided by MV diameter in normal, renovascular disease (RVD), and RVD+ELP-VEGF treated kidneys. *$p<0.05$ vs. Normal; †$p<0.05$ vs. RVD.

FIG. 10 includes bar graphs and tabular data demonstrating that ELP-VEGF is superior to unmodified VEGF at restoring renal function and microvascular density in the swine model of renal artery stenosis. Comparisons between intra-renal unbound VEGF vs. ELP-VEGF therapy on: Top—basal stenotic kidney RBF and GFR, expressed as % change compared to pre-treatment values; Middle—RBF and GFR responses to intra-renal infusion of acetylcholine; Bottom—effects of the treatments on cortical and medullary MV density (3D micro-CT reconstruction, divided by MV diameter) in renovascular disease (RVD)+VEGF and RVD+ELP-VEGF treated kidneys. †$p<0.05$ vs. RVD/RVD+VEGF; ‡$p<0.05$ vs. 6 weeks; ‡‡$p<0.05$ vs. baseline; #$p=0.09$ vs. RVD.

FIG. 11 includes Western blot data and bar graphs demonstrating that Intra-renal administration of ELP-VEGF improved the expression of angiogenic factors and promoters of mobilization and homing of progenitor cells in the stenotic kidney. Representative renal protein expression (top, 2 bands per group) of vascular endothelial growth factor (VEGF), its receptor Flk-1, phosphorylated (p)-akt, angiopoietin (Ang)-1 and -2, Tie-, angiostatin (angio), stromal-derived factor (SDF)-1 and its receptor CXCR4, and quantification (bottom) in normal, renovascular disease (RVD), and RVD+ELP-VEGF treated kidneys. *$p<0.05$ vs. Normal; †$p<0.05$ vs. RVD.

FIG. 12 includes Western blot and histological data showing that intra-renal administration of ELP-VEGF reduced renal fibrogenic activity and attenuated podocyte damage and fibrosis in the stenotic kidney. Top: Representative renal protein expression (2 bands per group) and quantification of transforming growth factor (TGF)-β, smads-4-7, matrix metalloproteinases (MMP)-2 and its inhibitor TIMP-1 in normal, renovascular disease (RVD), and RVD+ELP-VEGF treated kidneys. Middle: Representative pictures (from stenotic kidneys) of the glomeruli (×40), showed as examples to illustrate podocin immunoreactivity (black arrows). Bottom: Representative trichrome pictures (from stenotic kidneys) of the glomeruli and tubules, and tubule-interstitial regions (×20, showed as examples to illustrate renal damage). *$p<0.05$ vs. Normal; †$p<0.05$ vs. RVD.

FIG. 13 includes and image and a graph showing the effect of IV ELP-VEGF on renal function in RVD. A. Stenotic vs. contralateral kidney after 10 weeks of RVD (4 weeks after IV ELP-VEGF). B. Change in RBF and GFR after IV ELP-VEGF. C. Micro-CT quantification of renal MV density after IV ELP-VEGF. Intra-venous ELP-VEGF improved renal function and MV density of the stenotic kidney. *$p<0.05$ vs. Normal; †$p<0.05$ vs. RVD.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. Further, while the terms used herein are believed to be well-understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about" Accordingly, unless indicated to the contrary, the numerical parameters set forth in this specification and claims are approximations that can vary depending upon the desired properties sought to be obtained by the presently-disclosed subject matter.

The presently-disclosed subject matter relates to a composition and method for therapeutic agent delivery for treatment of kidney diseases. More particularly, the presently-disclosed subject matter relates to a composition comprising an elastin-like polypeptide (ELP) coupled to a kidney targeting agent and a therapeutic agent or agents, and a method of delivering the composition to a subject in need thereof.

As used herein, the term "elastin-like polypeptide" or "ELP" refers to a synthetic protein containing structural peptide units, which may be repeating units, structurally related to, or derived from, sequences of the elastin protein. ELP is a macromolecular carrier that has several advantages. It is an inert and biodegradable macromolecule, giving it a good pharmacokinetic profile and very low immunogenicity. Also, as opposed to chemically synthesized polymers, ELP is expressed in and easily purified from *E. coli*. Further, the sequence of a particular ELP can be controlled such that it is possible to generate chimeras of ELP fused to therapeutic proteins or peptides or to add reactive sites for attachment of therapeutic agents. Such ELP chimeras provide certain therapeutic advantages to the therapeutic agent, such as comparatively better stability, solubility, bioavailability, half-life, persistence, and/or biological action of the therapeutic proteinaceous component or attached small molecule drug.

In some embodiments, the presently-disclosed subject matter provides a kidney targeted drug delivery system composed of a biopolymer carrier modified with a kidney targeting agent and a drug binding domain or a directly fused therapeutic peptide or protein. The kidney targeted drug carrier consists of one of several targeting peptides that confer kidney-specific delivery fused to a biopolymer based on elastin-like polypeptide (ELP) [1-3]. In some embodiments, the ELP domain consists of repeating units of the GVPGX motif, in which X can be any amino acid except proline. In some embodiments, a drug binding domain and/or a therapeutic peptide or protein is also fused to the ELP biopolymer. In some embodiments, the drug binding domain consists of a region containing multiple cysteine or lysine residues that can be used for covalent attachment of drugs. In some embodiments, in addition to covalent drug attachment, the therapeutic domain might contain therapeutic peptides or proteins designed to intervene in disease processes of the kidney.

When all domains are included in the same molecule, the targeting domain increases kidney deposition and confers kidney specificity, the ELP biopolymer provides mass that confers protection from degradation and rapid renal clearance, and the therapeutic domain and/or drug binding domain provides a mechanism for intervening in disease processes of the kidney. ELPs can be fused to virtually any therapeutic compound by simple molecular biology techniques. Thus, determining the feasibility of using ELP technology for renal therapy could have clinical ramifications that go beyond chronic RVD and may extend to CKD from different etiologies.

In some embodiments, the presently disclosed subject matter provides a composition comprising an elastin-like polypeptide (ELP), a kidney targeting agent coupled to the ELP, and a therapeutic agent and/or a drug binding domain coupled to the ELP. In some embodiments, the presently disclosed subject matter further includes a pharmaceutically acceptable carrier. In some embodiments, the ELP includes an amino acid sequence having at least about 5 repeats of the amino acid sequence GVPGX (SEQ ID NO: 1), and the composition enhances the deposition and retention of the therapeutic agent in the kidney relative to the non-conjugated therapeutic. In some embodiments, the ELP includes an amino acid sequence comprising about 5 repeats to about 320 repeats of the amino acid sequence GVPGX. In some embodiments, X in the sequence GVPGX is any amino acid except proline. In some embodiments, X in the amino acid sequence GVPGX is Val, Ala, and Gly in a ratio range of about 0-1:0-8:0-8.

The terms "polypeptide", "protein", and "peptide", which are used interchangeably herein, refer to a polymer of the protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The term "kidney targeting agents" refers to short peptides designed to have specificity for the vascular beds or other cell types of specific organs such as kidney.

The term "therapeutic agent" and the like is used herein to refer to substances that can alter, inhibit, activate, catalyze, or otherwise affect a biological or chemical event in a subject. In some embodiments a therapeutic agent has the effect of treating a disease, condition, or disorder in a subject, and possibly in the kidney of a subject. Exemplary active agents include, but are not limited to, enzymes, organic catalysts, ribozymes, organometallics, proteins, glycoproteins, peptides, polyamino acids, antibodies, nucleic acids, steroidal molecules, antibiotics, antibacterial agents, anti-inflammatory agents, antivirals, antimycotics, anticancer agents, analgesic agents, antirejection agents, immunosuppressants, cytokines, carbohydrates, oleophobics, lipids, pharmaceuticals (i.e., drugs; including small molecules), chemotherapeutics, and combinations thereof.

Non-limiting examples of the ELP sequences include an amino acid sequence in which X in the GVPGX sequence is Val, Ala, and Gly in a 1:8:7 ratio (SEQ ID NO: 2), Gly (SEQ ID NO: 3), Val, Ala, and Gly in a 1:4:3 ratio (SEQ ID NO: 4), or a combination thereof.

Additionally, non-limiting examples of the kidney targeting agents include a kidney targeting peptide (SEQ ID NO: 5), a kidney targeting peptide (SEQ ID NO: 6), a Tat peptide (SEQ ID NO: 7), a SynB1 peptide (SEQ ID NO: 8), or a combination thereof.

Moreover, non-limiting examples of the drug binding domain includes repeats of the sequence GGC (SEQ ID NO: 9), the sequence GC (SEQ ID NO: 10), the sequence GGK (SEQ ID NO: 11), and the sequence GK (SEQ ID NO: 12).

Further provided in some embodiments of the presently disclosed subject matter, is a therapeutic agent includes at least one growth factor. In some embodiments, the growth factor includes VEGF, HGF, b-FGF, TGF-β, and HIF. In some embodiments, the therapeutic agent includes a VEGF selected from $VEGF_{121}$, $VEGF_{165}$, $VEGF_{189}$, $VEGF_{206}$, VEGF-A, VEGF-B, VEGF-C, VEGF-D, VEGF-E, and P1GF.

The term "pharmaceutically acceptable carrier" refers to sterile aqueous or nonaqueous solutions, dispersions, suspensions or emulsions, as well as sterile powders for reconstitution into sterile solutions or dispersions just prior to use. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Depending upon the ratio of drug to polymer and the nature of the particular polymer employed, the rate of drug release can be controlled. The formulations can be sterilized, for example, by filtration through a bacterial-retaining filter or by incorporating sterilizing agents in the form of sterile solid compositions which can be dissolved or dispersed in sterile water or other sterile injectable media just prior to use.

Further, in some embodiments, the presently-disclosed subject matter provides a method of delivering a therapeutic agent to a subject in need thereof. The method includes administering to the subject an effective amount of a composition. The composition includes an elastin-like polypeptide (ELP), a kidney targeting agent coupled to the ELP, and a therapeutic agent and/or a drug binding domain coupled to the ELP. In some embodiments, the ELP includes an amino acid sequence having at least about 5 repeats of the amino acid sequence GVPGX (SEQ ID NO: 1), and the composition enhances the deposition and retention of the therapeutic agent in the kidney relative to the non-conjugated therapeutic. In some embodiments, the ELP includes an amino acid sequence comprising about 5 repeats to about 320 repeats of the amino acid sequence GVPGX, and X in the sequence GVPGX is any amino acid except proline. In some embodiments, the X in the amino acid sequence GVPGX is Val, Ala, and Gly in a ratio range of about 0-1:0-8:0-8. In some embodiments, the ELP includes the amino acid sequence GVPGX, and X is Val, Ala, and Gly in a 1:8:7 ratio (SEQ ID NO: 2) repeated between 5 and 320 times. In some embodiments, the ELP comprises the amino acid sequence GVPGX, and wherein X is Gly (SEQ ID NO: 3) repeated between 5 and 320 times. In some embodiments, the ELP comprises the amino acid sequence GVPGX, and X is Val, Ala, and Gly in a 1:4:3 ratio (SEQ ID NO: 4) repeated between 5 and 320 times.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts.

Further provided, in some embodiments of the presently disclosed subject matter, is a targeting agent that is used to increase kidney deposition and specificity. The incorporation of the targeting agent increases kidney deposition and specificity of the delivered therapeutic agent and/or a drug binding domain. In some embodiments, the kidney targeting agent is a kidney targeting peptide having SEQ ID NO: 5. In some embodiments, the kidney targeting agent is a peptide having SEQ ID NO: 6. In some embodiments, the kidney targeting agent is a Tat peptide having SEQ ID NO: 7. In some embodiments, the kidney targeting agent is a SynB1 peptide having SEQ ID NO: 8. In some embodiments, non-limiting examples of the drug binding domain includes repeats of the sequence GGC (SEQ ID NO: 9), repeats of the sequence GC (SEQ ID NO: 10), repeats of the sequence GGK (SEQ ID NO: 11), and repeats of the sequence GK (SEQ ID NO: 12). In some embodiments, the therapeutic agent includes at least one growth factor selected from the group consisting of VEGF, HGF, b-FGF, TGF-β, and HIF. Non-limiting examples of VEGF include $VEGF_{121}$, $VEGF_{165}$, $VEGF_{189}$, $VEGF_{206}$, VEGF-A, VEGF-B, VEGF-C, VEGF-D, VEGF-E, and P1GF. In some embodiments, the composition is administered intra-renally, intravenously, intraperitoneally, orally, intranasally, or subcutaneously.

In this regard, the term "administer" refers to any method of providing a compound or composition thereof to a subject. In some embodiments, suitable methods for administering a therapeutic composition in accordance with the methods of the presently-disclosed subject matter may include, but are not limited to, intra-renal administration, intravenous administration, intraperitoneal administration, oral administration, intranasal administration, subcutaneous administration, systemic administration, parenteral administration (including intravascular, intramuscular, and/or intraarterial administration), buccal delivery, rectal delivery, inhalation, intratracheal installation, surgical implantation, transdermal delivery, local injection, and hyper-velocity injection/bombardment.

Further provided, in some embodiments of the presently-disclosed subject matter are methods for the treatment of various diseases and disorders using the exemplary ELP-therapeutic agent-containing compositions described herein. In some embodiments, the presently-disclosed subject matter includes a method of treating a kidney disease or disorder in a subject wherein the subject is administered an effective amount of a composition comprising an ELP coupled to a kidney targeting agent and a therapeutic agent and/or a drug binding protein. In some embodiments, the ELP includes an amino acid sequence having at least about 5 repeats of the amino acid sequence GVPGX (SEQ ID NO: 1), and the composition enhances the deposition and retention of the therapeutic agent in the kidney relative to the non-conjugated therapeutic. Exemplary diseases or disorders that can be treated in accordance with the presently-disclosed subject matter include, but are not limited to, Chronic kidney disease (CKD), Chronic renal vascular disease (RVD), end-stage renal disease.

In some embodiments the method for administering the present compounds and compositions further include treating a disease or condition in the subject. The terms "treatment" or "treating" refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Furthermore, the term "subject" is inclusive of both human and animal subjects. Thus, veterinary uses are provided in accordance with the presently disclosed subject matter and the presently-disclosed subject matter provides methods for preventing oxidative damage in mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The presently-disclosed subject matter is further illustrated by the following specific but non-limiting examples. The following examples may include compilations of data that are representative of data gathered at various times during the course of development and experimentation related to the present invention.

EXAMPLES

Example 1

Targeting Peptides Increase Total Renal Deposition and Enhance the Renal Specificity of ELP Biodistribution A biodistribution study was performed to determine whether increasing ELP levels in the kidneys using targeting peptides was possible. The ELP molecule was fused to one of two cell penetrating peptides (CPPs) (SynB1 and Tat [4, 5] or to a peptide found to have specificity for the kidney (Kidney Targeting Peptide. KTP [6]). Each polypeptide was labeled with a fluorophor and administered by IV injection at a dose of 100 mg/kg in hairless Sprague Dawley rats. The whole-body fluorescence of the animals throughout the experiment is measured by in vivo imaging. As shown in FIG. 1, when the untargeted ELP carrier was injected, the fluorescence spread throughout the body and reached a peak intensity approximately 1 hour after the injection, then the fluorescence level slowly decreased. In contrast, the SynB1-ELP and the KTP-ELP polypeptides achieved much higher levels throughout the body, and the levels were just beginning to peak four hours after the injection. These data reveal that the use of the targeting peptides increases extravasation and tissue uptake of the drug carrier and therefore slows its clearance from the body tissues.

The whole-body in vivo fluorescence provides a measurement of total tissue polypeptide levels, but it cannot resolve the individual organ biodistribution. In order to measure the biodistribution, the major organs were removed, and polypeptide levels were determined by quantitative whole organ ex vivo imaging four hours after the injection. As shown in FIG. 2, the unmodified ELP accumulated most highly in the kidney and the liver. When the ELP was modified with the cell penetrating peptides or the KTP, the kidney levels increased dramatically (over five-fold, FIG. 2B). Both cell penetrating peptides and the KTP achieved similar kidney levels. However, when kidney specificity was assessed by measuring the kidney:liver and the kidney:heart ratios, the KTP proved to be by far the most specific (FIGS. 2C and D). In fact, KTP-ELP accumulated in the kidneys at levels 15-fold higher than in the liver and as much as 150-fold higher than in other organs including the heart, brain, and spleen. These data demonstrate that KTP is an effective targeting agent for increasing both total renal accumulation and renal specificity of the ELP drug carrier, and they are the first demonstration of the use of targeting peptides to achieve kidney-specific delivery of the ELP carrier.

In addition to the whole-organ ex vivo imaging, the kidneys were frozen and sectioned to determine the intrarenal distribution of the polypeptides. Fluorescence slide scanning revealed that all polypeptides were mostly confined to the renal cortex (FIG. 3A). Also, consistent with the whole-organ imaging, SynB1-ELP, Tat-ELP, and KTP-ELP accumulated to very high levels relative to the untargeted ELP biopolymer. When examined microscopically (FIG. 3B), KTP-ELP was localized around the nephron (marked by synaptopodin staining) and was detectable in both the blood vessel walls (as indicated by CD31 staining) and in the surrounding proximal and distal tubules. Images taken in the outer medulla and co-stained with calbindin to mark the collecting ducts also showed high levels of KTP-ELP within the ductal epithelial cells. SynB1-ELP and Tat-ELP had very similar intrarenal distributions (data not shown).

To insure that the ability of KTP to target ELP to the kidneys was not specific to rats, a similar experiment was conducted in swine. Domestic crossbred female pre-juvenile pigs (sus scrofa domestica) were adminstered ELP or KTP-ELP (n=3 pigs/agent) by IV injection. Ex vivo quantitative fluorescence histology was performed as described above. As shown in FIG. 4, KTP-ELP accumulated in the swine kidney at levels 5.4 fold higher than the untargeted ELP, and kidney KTP-ELP levels were 4.8-fold higher than liver, almost two-fold higher than lung, and over 50-fold higher than heart and spleen. These data demonstrate that KTP is effective for kidney targeting in a predictive preclinical model and is not species specific.

We also sought to determine if KTP could enhance ELP binding to primary human renal cells and to identify which cell type KTP has affinity for. Primary human glomerular microvascular endothelial cells (HOME), primary human podocytes, and primary human renal proximal tubule epithelial cells (HRPTEpC) were cultured in vitro and exposed to 10 µM ELP or KTP-ELP. Cells were also exposed to the cell penetrating peptide—fused ELPs SynB1-ELP and Tat-ELP as comparators. As shown in FIG. 5. KTP enhanced ELP binding to all renal cell types. Binding was increased 3 fold in HGME, 1.7 fold in podocytes, and 3 fold in HRPT-EpC by KTP-ELP relative to ELP control. This was in contrast to the CPP-fused ELPs. Tat only enhanced ELP binding to HRPTEpC and actually reduced binding to podocytes. SynB1 only enhanced ELP binding to HGME cells and also reduced binding to podocytes (FIG. 5A). We also tested whether KTP-ELP had any toxicity to the human cell lines. Each cell line was incubated with ELP, SynB1-ELP, Tat-ELP, or KTP-ELP at concentrations up to 40 µM for 72 h, and cell number was determined using the MTS assay. KTP showed no toxicity to any cell line tested, and it even stimulated proliferation of HRPTEpC (FIG. 5B). In contrast, Tat-ELP was toxic HGME cells. SynB1-ELP showed no cytotoxicity. These data demonstrate that KTP has affinity for several renal cell lines, and, in contrast to CPPs, it increases ELP binding to all renal cell types tested.

Example 2

ELP-Fused Vascular Endothelial Growth Factor (VEGF) Deposits in the Kidney and Improves Renal Function in a Swine Model of Renovascular Disease Chronic kidney disease (CKD) is a progressive disorder affecting almost 14% of the general population, and the prevalence of this disease has continuously grown over the past 2 decades [7]. CKD is an independent risk factor for cardiovascular morbidity and mortality, as patients with diagnosed cardiovascular disease show a staggering 40.8% prevalence of CKD, a number that has doubled in less than 20 years [7]. Patients with CKD have higher rates of hospitalization, greater mortality, shorter life expectancy, and their healthcare costs are up to 5 times more expensive than non-CKD patients, which represent an enormous burden to the healthcare budget. Thus, treatments to slow, halt, or reverse the progression of CKD could have a significant impact.

Chronic RVD can deteriorate renal function and lead to CKD and end-stage renal disease. It affects between 9-11% of the general population, but this number goes up in patients with diagnosed coronary artery or peripheral vascular disease (about 30%), and are much higher in older patients (up to 60% in patients>65 years) [8-10]. The main cause of RVD is renal artery stenosis, often due to atherosclerosis. Although the vascular obstruction is the initial and possibly main instigator of renal injury, therapeutic strategies that aim to resolve the vascular stenosis such as renal angioplasty and stenting are effective in recovering renal function in less than half of the cases. The disparity between technical success and outcomes has served as the impetus for numerous trials to assess the efficacy of medical therapy vs. interventions in this disease, focusing in two major end points: reduction of hypertension and recovery of renal function. Nevertheless, the outcomes of RVD are still poor. Although numerous trials have been critiqued because of flaws in design and follow up, the results weighed more towards the conclusion that there are no major benefits achieved by renal angioplasty compared to medical treatment that would justify the risk of revascularization procedures [11]. Consequently, there is a noticeable lack of consensus regarding the best therapeutic strategy for these patients. Hence, more effective treatments are needed and the technology described within represents a new therapeutic strategy that has not been previously tested for renal therapy.

Damage of the small vessels in the kidney is a common pathological feature in CKD and end stage renal disease irrespective of the cause. Furthermore, major cardiovascular factors and causes of CKD such as hypertension or diabetes have been shown to associate with intra-renal microvascular (MV) rarefaction that is observed before deterioration of renal function. These support the notion of a potential cause-effect relationship and suggest a pathophysiological role of MV damage on the progression of renal dysfunction. Over the past 14 years, a unique swine model of RVD was developed that mimics the progressive nature of renal injury, hypertension, and cardiovascular risk found in humans with RVD. Moreover, physiological imaging techniques were developed and validated using high-resolution computerized tomography (CT) to measure renal regional volumes, total renal blood flow (RBF), glomerular filtration rate (GFR), tubular dynamics, and endothelial function; and micro-CT to study the 3D architecture of the renal microcirculation in situ. These techniques allow us to non-invasively and serially follow the time course of the deterioration of the kidney in an integrative fashion and with previously unavailable accuracy. Progressive loss of renal function and tissue damage in RVD is accompanied by marked and progressive renal microvascular damage and loss in the stenotic kidney (evident in both renal cortex and medulla), which is mediated by a progressive decrease in renal expression and availability of VEGF and a defective renal angiogenesis and vascular repair [12-15].

ELP-VEGF is retained in the kidney after intrarenal administration in the pig. To determine if the ELP-delivered VEGF could be retained in the kidney in the swine RVD model, a biodistribution study in the pig was conducted. Three pigs (average weight 49.2 kg) were administered fluorescently labeled ELP-VEGF by direct intrarenal injection under fluoroscopy guidance. A balloon catheter was inflated for three minutes following the injection, then the balloon was deflated to allow blood to circulate through the kidney. Blood was sampled from the jugular vein at fixed time-points, and plasma fluorescence measurements were taken to monitor ELP-VEGF levels. The distribution phase half-life was 2.95 minutes and the terminal plasma half-life was 810.1 minutes (FIG. 6). Four hours after injection, the pigs were sacrificed and the organs analyzed by ex vivo fluorescence imaging. As shown in FIG. 7, the injected kidney retained the ELP-VEGF, showing tissue levels nearly three fold higher than the contralateral kidney or any other organ. Some protein did enter systemic circulation, as evidenced by its detection in the contralateral kidney and liver. However, these results demonstrate that intrarenal administration is a viable route for delivery of ELP-VEGF, and kidney levels will be increased further when the ELP-VEGF is fused to the KTP.

ELP-VEGF is equally as active as free vegf in primary human glomerular microvascular endothelial (hgme) cells. Primary Human Glomerular Microvascular Endothelial (HGME) cells were used to insure the signaling properties of VEGF were retained even after fusion to the ELP carrier. As shown in FIG. 8A, both unbound VEGF and ELP-VEGF stimulated proliferation of HOME cells, while the ELP polypeptide alone had no effect on HGME proliferation. Furthermore, no significant differences were seen in the potency of the unbound cytokine and the ELP-fused VEGF, suggesting that the ELP-fused VEGF is still able to bind its receptor. To test this further, HGME cells were used in to a tube formation assay on growth factor reduced Matrigel. As shown in FIG. 8B, very little tube formation was observed on this matrix without additional stimulation. However, when the media was supplemented with unbound VEGF or ELP-VEGF, tube formation was significantly induced. Quantification of tubes per visual field showed that both unbound VEGF and ELP-VEGF significantly induced tube formation relative to untreated cells (FIG. 8C). There were also more average tubes per field in the ELP control-treated samples, though the difference did not reach statistical significance. Finally, to assess the ability of ELP-VEGF to serve as a chemokine for HGME cells, a Matrigel migration assay was used. As shown in FIG. 8D and quantified in FIG. 8E, both unbound VEGF and ELP-VEGF strongly induced HGME cell migration through Matrigel, while the control ELP had no effect. Again, there was no difference in potency between VEGF and ELP-VEGF.

Single-dose intra-renal elp-vegf causes improvement in renal function in a swine model of chronic rvd. To determine whether administration of ELP-VEGF into the stenotic kidney has an impact on renal function and microvascular architecture, 7 pigs were treated after 6 weeks of RVD with a single infusion of ELP-VEGF (100 µg/kg). An additional 7 pigs with RVD received placebo and were used as controls. Single-kidney function was quantified in vivo in all pigs before and 4 weeks after treatments/placebo. Pigs were observed for a total of 10 weeks and then euthanized. Kidneys were then removed and micro CT studies (to quantify the impact of ELP/placebo on the renal microvasculature) and protein expression studies performed. It was observed that administration of ELP-VEGF significantly improved renal function compared to placebo (FIG. 9A, top). The improvement was specific to ELP-VEGF, as the ELP control polypeptide had no effect on renal function. The stenotic kidney showed a significant reduction in cortical and medullary microvascular density accompanied by substantial microvascular remodeling compared to normal controls (FIG. 9A, bottom). Notably, intra-renal ELP-VEGF significantly improved both cortical and medullary microvascular density and remodeling of small and large microvessels (0-500 µm in diameter), which was evident throughout the renal parenchyma (FIG. 9B).

ELP-VEGF is more effective than unconjugated vegf for improvement of renal function. A single intra-renal administration of free $VEGF_{121}$ significantly improved stenotic RBF but not GFR (p<0.05 and p=NS, respectively, vs.

pre-treatment values) and the magnitude of those changes was significantly less compared to ELP-VEGF therapy (FIG. 10, top). Furthermore, intra-stenotic kidney infusion of acetylcholine (quantified at 10 weeks) improved RBF but not GFR in free VEGF treated kidneys whereas both RBF and GFR were improved in after ELP-VEGF (FIG. 10, middle). Finally, free VEGF therapy improved MV density only in those cortical microvessels under 200 µm in diameter and not in larger microvessels (200-500 µm in diameter, FIG. 10, bottom. Overall, these findings strongly support a superior efficacy of ELP-VEGF therapy over unconjugated VEGF.

ELP-VEGF activates VEGF signaling in the stenotic kidney. Kidneys from the efficacy study were examined by Western blot to confirm activation of VEGF signaling at the experimental endpoint. Expression of VEGF, the receptor Flk-1, angiopoietin (Ang)-1 and -2 and the Tie-2 receptor were significantly reduced in RVD but largely restored and accompanied by improved expression of phosphorylated (p)-akt, stromal-derived factor (SDF)-1 and the CXCR4 receptor, and attenuated expression of anti-angiogenic angiostatin (angio) after ELP-VEGF therapy, suggesting a pro-angiogenic milieu in the stenotic kidney of ELP-VEGF treated pigs (FIG. 11).

ELP-VEGF reduces inflammatory activity and fibrotic damage in the stenotic kidney. ELP-VEGF therapy decreased the renal concentration of tumor necrosis factor (TNF)-$\alpha$ (Untreated pigs 9.8±1.4 pg/mg tissue; RVD 19.4±0.6 pg/mg tissue; RVD±ELP-VEGF 13.4±3.2 pg/mg tissue, p<0.05), and attenuated the expression of pro-fibrotic transforming growth factor (TGF)-$\beta$, smad-4, and tissue inhibitor of matrix-metalloproteinase (TIMP)-1, whereas improved smad-7 and matrix-metalloproteinase (MMP)-2 compared to untreated RVD, suggesting a potential decrease in pro-inflammatory, pro-fibrotic, and tissue remodeling activity (FIG. 12, top). Furthermore, ELP-VEGF therapy improved glomerular expression of podocin (FIG. 12, middle) and reduced nephrinuria, suggesting protection of podocytes. Glomerulosclerosis and tubule-interstitial fibrosis (7.3±0.01 and 9.3±0.04%, respectively, p<0.05 vs. Normal) were significantly reduced (2.3±0.04 and 3.4±0.1%, respectively, p<0.05 vs. RVD and Normal) after ELP-VEGF therapy (FIG. 12, bottom). Similarly, MV media-to-lumen ratio (0.34±0.01, p<0.05 vs. Normal) was improved after ELP-VEGF therapy (0.18±0.05, p<0.05 vs. RVD, p=NS vs. Normal), suggesting attenuated MV remodeling in addition to the improvements in MV rarefaction.

This study supports the feasibility of ELP-VEGF therapy and suggests therapeutic effects of this intervention.

Single-dose systemically-delivered ELP-VEGF improves renal function in a swine model of chronic RVD. Since ELPs have high affinity for renal tissue, preliminary studies were performed to determine whether a systemic administration may protect the kidney and improve renal function. To test this, 4 pigs with RVD were observed for 6 weeks, stenotic kidney function quantified, and then 2 of them treated with an intra-venous (IV) injection of ELP-VEGF via an ear vein cannula. Animals were observed for 4 additional weeks, and renal function was re-evaluated, observing that RBF and GFR in the stenotic kidney of treated pigs were improved by over 70% compared to pre-treatment function, as cortical MV rarefaction diminished (FIG. 13). These data suggested renoprotective effects of ELP-VEGF even using a systemic route.

Throughout this document, various references are mentioned. All such references are incorporated herein by reference, including the references set forth in the following list.

REFERENCES

1. Kagan H M, Tseng L, Trackman P C, et al. (1980) Repeat polypeptide models of elastin as substrates for lysyl oxidase. J Biol Chem 255:3656-9.
2. Luan C H, Parker T M, Prasad K U, Urry D W (1991) Differential scanning calorimetry studies of NaCl effect on the inverse temperature transition of some elastin-based polytetra-, polypenta-, and polynonapeptides. Biopolymers 31:465-75. doi: 10.1002/bip.360310502
3. McPherson D T, Morrow C, Minehan D S, et al. (1992) Production and purification of a recombinant elastomeric polypeptide, G-(VPGVG)19-VPGV, from *Escherichia coli*. Biotechnol Prog 8:347-52. doi: 10.1021/bp00016a012
4. Rousselle C, Clair P, Lefauconnier J M, et al. (2000) New advances in the transport of doxorubicin through the blood-brain barrier by a peptide vector-mediated strategy. Mol Pharmacol 57:679-86.
5. Vives E, Brodin P. Lebleu B (1997) A truncated HIV-1 Tat protein basic domain rapidly translocates through the plasma membrane and accumulates in the cell nucleus. J Biol Chem 272:16010-7.
6. Pasqualini R, Ruoslahti E (1996) Organ targeting in vivo using phage display peptide libraries. Nature 380:364-6. doi: 10.1038/380364a0
7. National Institutes of Health, National Institute of Diabetes and Digestive and Kidney Diseases (2013) U.S. Renal Data System, USRDS 2013 Annual Data Report: Atlas of Chronic Kidney Disease and End-Stage Renal Disease in the United States.
8. Ritchie J, Green D, Chrysochou C, et al. (2014) High-risk clinical presentations in atherosclerotic renovascular disease: prognosis and response to renal artery revascularization. Am J Kidney Dis Off J Natl Kidney Found 63:186-197. doi: 10.1053/j.ajkd.2013.07.020
9. Textor S C, Lerman L O (2014) Reality and renovascular disease: when does renal artery stenosis warrant revascularization? Am J Kidney Dis Off J Natl Kidney Found 63:175-177. doi: 10.1053/j.ajkd.2013.11.004
10. Textor S C, Misra S, Oderich G S (2013) Percutaneous revascularization for ischemic nephropathy: the past, present, and future. Kidney Int 83:28-40. doi: 10.1038/ki.2012.363
11. Cooper C J, Murphy T P, Cutlip D E, et al. (2014) Stenting and medical therapy for atherosclerotic renal-artery stenosis. N Engl J Med 370:13-22. doi: 10.1056/NEJMoa1310753
12. Chade A R, Kelsen S (2010) Renal microvascular disease determines the responses to revascularization in experimental renovascular disease. Circ Cardiovasc Interv 3:376-383. doi: 10.1161/CIRCINTERVENTIONS.110.951277
13. Chade A R, Kelsen S (2012) Reversal of renal dysfunction by targeted administration of VEGF into the stenotic kidney: a novel potential therapeutic approach. Am J Physiol Ren Physiol 302:F1342-50. doi: 10.1152/ajprenal.00674.2011
14. Iliescu R, Fernandez S R, Kelsen S, et al. (2010) Role of renal microcirculation in experimental renovascular disease. Nephrol Dial Transplant Off Publ Eur Dial Transpl Assoc—Eur Ren Assoc 25:1079-1087. doi: 10.1093/ndt/gfp605
15. Chade A R, Zhu X, Lavi R, et al. (2009) Endothelial progenitor cells restore renal function in chronic experimental renovascular disease. Circulation 119:547-557. doi: 10.1161/CIRCULATIONAHA.108.788653

We claim:

1. A pharmaceutical composition, comprising:
a therapeutically effective amount of elastin-like polypeptide (ELP) coupled to a therapeutic agent;
a drug binding domain coupled to the ELP; and
a pharmaceutically acceptable carrier;
wherein the ELP includes an amino acid sequence having at least 5 repeats of the amino acid sequence GVPGX (SEQ ID NO: 1);
wherein X in the sequence GVPGX (SEQ ID NO: 1) is any amino acid except proline;
wherein the drug binding domain does not bind the therapeutic agent and
wherein the therapeutically effective amount of the ELP coupled to the therapeutic agent improves the deposition and retention of the therapeutic agent in the kidney relative to a non-conjugated therapeutic.

2. The pharmaceutical composition of claim 1, wherein the therapeutic agent is VEGF, HGF, b-FGF, TGF-β, and HIF.

3. The pharmaceutical composition of claim 1, wherein the pharmaceutically acceptable carrier is for delivery intra-renally, intravenously, intraperitoneally, orally, intranasally, or subcutaneously.

4. The pharmaceutical composition of claim 1, further comprising a kidney targeting agent coupled to the ELP, wherein the pharmaceutical composition enhances the deposition and retention of the therapeutic agent in the kidney relative to the non-conjugated therapeutic.

5. The pharmaceutical composition of claim 1, wherein the ELP includes an amino acid sequence comprising 5 repeats to 320 repeats of the amino acid sequence GVPGX (SEQ ID NO: 1).

6. The pharmaceutical composition of claim 5, wherein the X in the amino acid sequence GVPGX (SEQ ID NO: 1) is Val, Ala, and Gly in a ratio range of 0-1:0-8:0-8.

7. The pharmaceutical composition of claim 6, wherein X is selected from Val, Ala, and Gly in a 1:8:7 ratio or 1:4:3 ratio, repeated between 5 and 320 times.

8. The pharmaceutical composition of claim 1, wherein the ELP is selected from amino acid sequences of SEQ ID NOs: 2, 3 and 4.

9. The pharmaceutical composition of claim 4, wherein the kidney targeting agent is selected from amino acid sequences of SEQ ID NOs: 5, 6, 7, and 8.

10. The pharmaceutical composition of claim 1, wherein the drug binding domain is selected from amino acid sequences of SEQ ID NOs: 9, 10, 11, and 12.

11. The pharmaceutical composition of claim 2, wherein the therapeutic agent is VEGF, and selected from $VEGF_{121}$, $VEGF_{165}$, $VEGF_{189}$, $VEGF_{206}$, VEGF-A, VEGF-B, VEGF-C, VEGF-D, VEGF-E, and PlGF.

12. The pharmaceutical composition of claim 1, wherein at least one element of the composition is coupled via a peptide, a non-cleavable modified peptide bond, a protease cleavable peptide linker, or an acid labile chemical linker.

13. A method of treating kidney disease in a subject in need thereof, comprising:
administering an effective amount of a pharmaceutical composition, comprising
an elastin-like polypeptide (ELP) coupled to a therapeutic agent, a drug binding domain coupled to the ELP, and a pharmaceutically acceptable carrier;
wherein the ELP includes an amino acid sequence having at least 5 repeats of the amino acid sequence GVPGX (SEQ ID NO: 1);
wherein X in the sequence GVPGX (SEQ ID NO: 1) is any amino acid except proline; and
wherein the drug binding domain does not bind the therapeutic agent.

14. The method of claim 13, wherein said administration is intra-renally, intravenously, intraperitoneally, orally, intranasally, or subcutaneously.

15. The method of claim 13, wherein the ELP includes an amino acid sequence comprising 5 repeats to 320 repeats of the amino acid sequence GVPGX (SEQ ID NO: 1).

16. The method of claim 13, wherein the X in the amino acid sequence GVPGX (SEQ ID NO: 1) is chosen from:
Val, Ala, and Gly in a ratio range of 0-1:0-8:0-8; or
Val, Ala, and Gly in a 1:8:7 ratio or 1:4:3 ratio, repeated between 5 and 320 times.

17. The method of claim 13, wherein the therapeutic agent comprises at least one growth factor selected from the group consisting of VEGF, HGF, b-FGF, TGF-β, and HIF.

18. The method of claim 17, wherein the therapeutic agent is VEGF.

19. The method of claim 18, wherein the VEGF is selected from $VEGF_{121}$, $VEGF_{165}$, $VEGF_{189}$, $VEGF_{206}$, VEGF-A, VEGF-B, VEGF-C, VEGF-D, VEGF-E, and PlGF.

20. The method of claim 13, wherein the kidney disease is selected from a group consisting of chronic kidney disease, chronic renal vascular disease, chronic renal vascular disease caused by renal artery stenosis, and end-stage renal disease.

21. The method of claim 13, wherein the pharmaceutical composition further comprises a kidney targeting agent (KTA) coupled to the ELP, and wherein the KTA coupled to the ELP of the pharmaceutical composition enhances the deposition and retention of the therapeutic agent in the kidney relative to a pharmaceutical composition without the KTA.

22. The pharmaceutical composition of claim 2, wherein the therapeutically effective amount of the ELP coupled to the therapeutic agent treats kidney disease in a subject.

23. The pharmaceutical composition of claim 22, wherein the kidney disease is selected from the group consisting of chronic kidney disease, chronic renal vascular disease, and end-stage renal disease.

24. A pharmaceutical composition, comprising:
a therapeutically effective amount of elastin-like polypeptide (ELP) coupled to a therapeutic agent, and a pharmaceutically acceptable carrier;
wherein the ELP includes an amino acid sequence having at least 5 repeats of the amino acid sequence GVPGX (SEQ ID NO: 1);
wherein X in the sequence GVPGX (SEQ ID NO: 1) is any amino acid except proline;
wherein the ELP is selected from amino acid sequences of SEQ ID NOs: 2, 3 and 4; and
wherein the therapeutically effective amount of the ELP coupled to the therapeutic agent improves the deposition and retention of the therapeutic agent in the kidney relative to a non-conjugated therapeutic.

* * * * *

UNITED STATES PATENT AND TRADEMARK OFFICE
CERTIFICATE OF CORRECTION

PATENT NO. : 10,322,189 B2
APPLICATION NO. : 15/517805
DATED : June 18, 2019
INVENTOR(S) : Alejandro R. Chade and Gene L. Bidwell, III Page 1 of 1

It is certified that error appears in the above-identified patent and that said Letters Patent is hereby corrected as shown below:

On the Title Page (72), Inventors:
Delete "Alejandro R. Chade, III, Brandon, MS" and replace with "Alejandro R. Chade, Brandon, MS"

Signed and Sealed this
Sixth Day of August, 2019

Andrei Iancu
*Director of the United States Patent and Trademark Office*